US010544185B2

United States Patent
Lv et al.

(10) Patent No.: US 10,544,185 B2
(45) Date of Patent: Jan. 28, 2020

(54) DEUTERATED CHENODEOXYCHOLIC ACID DERIVATIVE AND PHARMACEUTICAL COMPOSITION COMPRISING COMPOUND THEREOF

(71) Applicant: Suzhou Zelgen Biopharmaceuticals Co., Ltd., Kunshan Suzhou, Jiangsu (CN)

(72) Inventors: Binhua Lv, Jiangsu (CN); Zelin Sheng, Jiangsu (CN); Chengwei Li, Jiangsu (CN)

(73) Assignee: Suzhou Zelgen Biopharmaceuticals Co., Ltd., Kunshan, Suzhou, Jiangsu (CN)

( * ) Notice: Subject to any disclaimer, the term of this patent is extended or adjusted under 35 U.S.C. 154(b) by 0 days.

(21) Appl. No.: 15/551,224

(22) PCT Filed: Feb. 16, 2016

(86) PCT No.: PCT/CN2016/073891
§ 371 (c)(1),
(2) Date: Aug. 15, 2017

(87) PCT Pub. No.: WO2016/131414
PCT Pub. Date: Aug. 25, 2016

(65) Prior Publication Data
US 2018/0030083 A1 Feb. 1, 2018

(30) Foreign Application Priority Data
Feb. 16, 2015 (CN) .......................... 2015 1 0084738

(51) Int. Cl.
*C07J 9/00* (2006.01)
*A61K 31/575* (2006.01)
*A61K 45/06* (2006.01)
*C07B 59/00* (2006.01)

(52) U.S. Cl.
CPC ............. *C07J 9/005* (2013.01); *A61K 31/575* (2013.01); *A61K 45/06* (2013.01); *C07B 59/007* (2013.01); *C07B 2200/05* (2013.01)

(58) Field of Classification Search
CPC ....... A61K 31/575; A61K 45/06; C07J 9/005; C07B 59/007; C07B 2200/05
See application file for complete search history.

(56) References Cited

U.S. PATENT DOCUMENTS 6,376,531 B1 * 4/2002 Bell ...................... A61K 31/135
514/237.5
6,603,008 B1 * 8/2003 Ando ................... C07D 405/14
546/269.7

FOREIGN PATENT DOCUMENTS

| WO | WO9526325 | * | 10/1995 |
| WO | 02072598 A1 | | 9/2002 |
| WO | 2005082925 A2 | | 9/2005 |
| WO | 2010059859 A1 | | 5/2010 |
| WO | WO2013037482 | * | 3/2013 |
| WO | 2015061421 A1 | | 4/2015 |

OTHER PUBLICATIONS

Kushner et al., Pharmacological uses and perspectives of heavy water and deuterated compounds. Canadian Journal of Physiology and Pharmacology, vol. 77, pp. 79-88, 1999. (Year: 1999).*
Foster et al., Deuterium isotope effects in studies of drug metabolism. Trends in Pharmacological Sciences, vol. 5, pp. 524-527, 1984. (Year: 1984).*
Dyck et al., Effects of deuterium substitution on the catabolism of beta-phenylethylamine: An in vivo study. Journal of Neurochemistry, vol. 46, pp. 399-404, 1986. (Year: 1986).*
Int'l Search Report dated May 9, 2016 in Int'l Application No. PCT/CN2016/073891.
Jiang et al, "Application of Deuteration in Drug Research," Qilu Pharmaceutical Affairs, vol. 29, No. 11, pp. 682-684 (2010), English Abstract Only.

* cited by examiner

*Primary Examiner* — Barbara P Badio
(74) *Attorney, Agent, or Firm* — Panitch Schwarze Belisario & Nadel LLP

(57) ABSTRACT

Disclosed are deuterated chenodeoxycholic acid derivatives and pharmaceutical compositions containing the deuterated chenodeoxycholic acid derivatives. In particular, disclosed is a deuterated chenodeoxycholic acid derivative of formula (I), or a crystal form, pharmaceutically acceptable salt, hydrate or solvate thereof, and a pharmaceutical composition containing the same. The deuterated chenodeoxycholic acid derivatives of formula (I) can be used to treat and/or prevent diseases related to the farnesoid X receptor (FXR) and/or G-protein coupled bile acid receptor, such as nonalcoholic steatohepatitis, nonalcoholic fatty liver diseases, gallstones, primary biliary cirrhosis, and cirrhosis.

17 Claims, No Drawings

DEUTERATED CHENODEOXYCHOLIC ACID DERIVATIVE AND PHARMACEUTICAL COMPOSITION COMPRISING COMPOUND THEREOF

CROSS-REFERENCE TO RELATED APPLICATION

This application is a Section 371 of International Application No. PCT/CN2016/073891, filed Feb. 16, 2016, which was published in the Chinese language on Aug. 25, 2016 under International Publication No. WO 2016/131414 A1, and the disclosure of which is incorporated herein by reference.

FIELD OF THE INVENTION

The present invention belongs to the field of medicine. In particular, the present invention relates to novel deuterated chenodeoxycholic acid derivative thereof, and pharmaceutical composition comprising the compound.

BACKGROUND OF THE INVENTION

Farnesoid X receptor (FXR) is a member of the nuclear receptor family, which is mainly expressed in the intestinal system such as liver, small intestine and other, and involved in links such as bile acid metabolism and cholesterol metabolism. Bile acids have a variety of physiological functions, and play an important role in processes such as fat absorption, transport, distribution and dynamic balance of cholesterol. The farnesoid X receptor acts as a receptor for bile acids such as chenodeoxycholic acid and maintains the in vivo balance of bile acids by regulating the gene expression involved in bile acid metabolism. In addition, the farnesoid X receptor also plays an important role in the in vivo dynamic balance of glucose and insulin resistance. Thus, farnesoid X receptor agonists are expected to be used in the development of drugs for the treatment of nonalcoholic steatohepatitis, nonalcoholic fatty liver disease, gallstones, primary biliary cirrhosis, cirrhosis, liver fibrosis, diabetes, hypercholesterolemia, atherosclerosis, obesity, hypertriglyceridemia, etc.

Deoxycholic acid and its derivatives are a class of agonists of farnesoid X receptors. A series of chenodeoxycholic acid derivatives are disclosed in patents WO2010059859 and WO2005082925, wherein the compound obeticholic acid is a selective farnesoid X receptor agonist, which chemical name is 3α,7α-dihydroxy-6α-ethyl-5β-cholan-24-oic acid, which can be used in the treatment of non-alcoholic steatohepatitis and nonalcoholic fatty liver-related diseases. At present, obeticholic acid is in phase III clinical study.

Although obeticholic acid has a better clinical effect in improving liver inflammation and fibrosis levels, and has effects such as weight loss and increasing insulin sensitivity, etc, other side effects are also found, such as itching and the raise of low density lipoprotein level. Therefore, the search for farnesoid X receptor agonists selective as well as of high activity and safety is very challenging.

Accordingly, there remains a need in the art for the development of compounds of good activation effect for farnesoid X receptors or better pharmacodynamics/pharmacokinetic properties.

SUMMARY OF THE INVENTION

The object of the present invention is to provide a novel class of compounds having farnesoid X receptor activating activity and better pharmacodynamics/pharmacokinetic properties, and use thereof.

In the first aspect of the present invention, there is provided a deuterated chenodeoxycholic acid derivative represented by formula (I) or crystal form, pharmaceutically acceptable salts, hydrates or solvates thereof:

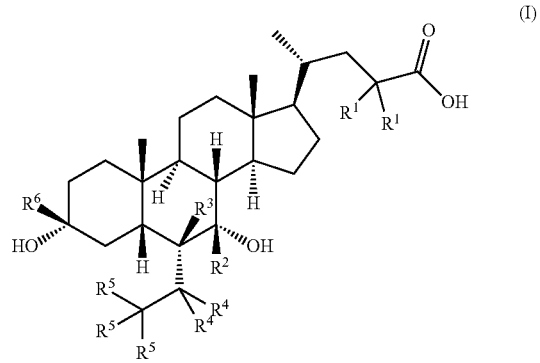

wherein:

$R^1$, $R^2$, $R^3$, $R^4$, $R^5$ and $R^6$ are each independently hydrogen or deuterium;

with the proviso that at least one of $R^1$, $R^2$, $R^3$, $R^4$, $R^5$ or $R^6$ is deuterium.

In another preferred embodiment, the deuterium isotope content of deuterium in the deuterium substituted position is at least greater than the amount of natural isotopic deuterium content (about 0.015%), preferably greater than 30%, more preferably greater than 50%, more preferably greater than 75%, more preferably greater than 95%, more preferably greater than 99%.

In another preferred embodiment, the compound of formula (I) contains at least one deuterium atom, more preferably two deuterium atoms, more preferably three deuterium atoms, more preferably five deuterium atoms, more preferably six deuterium atoms.

In another preferred embodiment, $R^1$ is hydrogen or deuterium.

In another preferred embodiment, $R^2$ is hydrogen or deuterium.

In another preferred embodiment, $R^3$ is hydrogen or deuterium.

In another preferred embodiment, $R^4$ and $R^5$ are independently selected from hydrogen or deuterium.

In another preferred embodiment, $R^6$ is hydrogen or deuterium.

In another preferred embodiment, $R^1$ is deuterium.

In another preferred embodiment, $R^2$ is deuterium.

In another preferred embodiment, $R^3$ is deuterium.

In another preferred embodiment, $R^4$ is deuterium and/or $R^5$ is deuterium.

In another preferred embodiment, $R^2$ is deuterium and/or $R^1$ is deuterium.

In another preferred embodiment, the compound is one of the following compounds, or the pharmaceutical acceptable salt thereof:

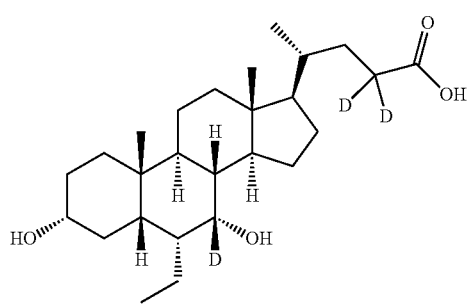
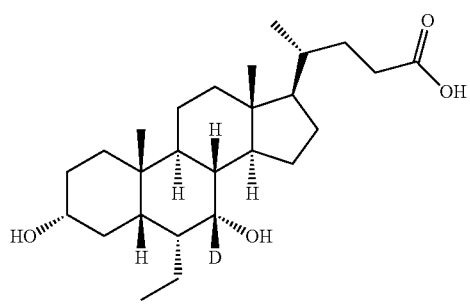
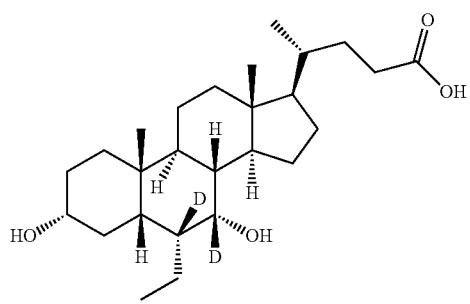
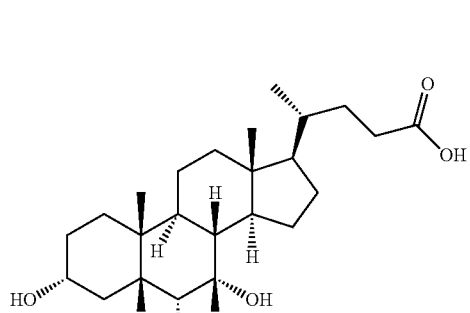
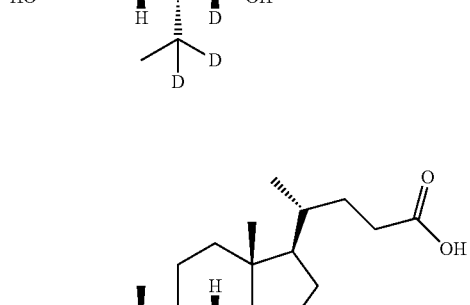
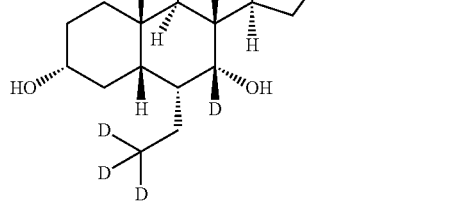
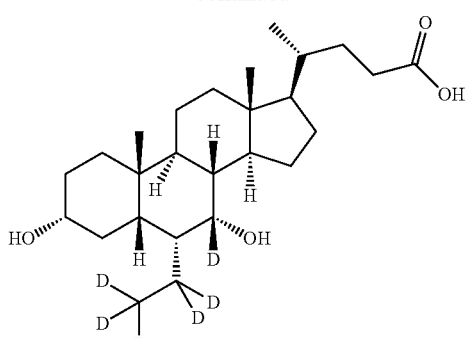
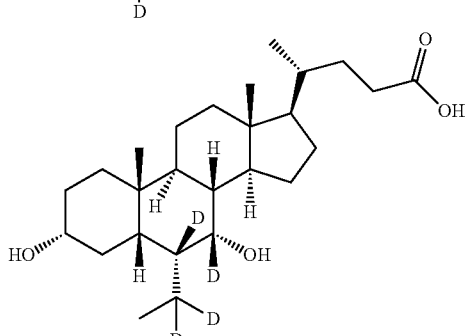
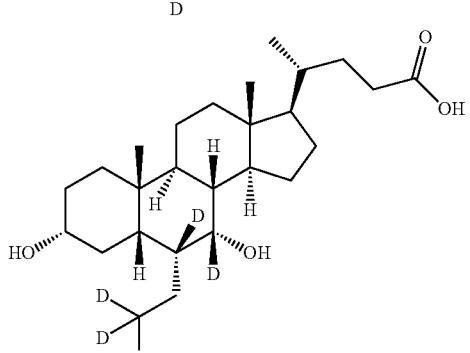
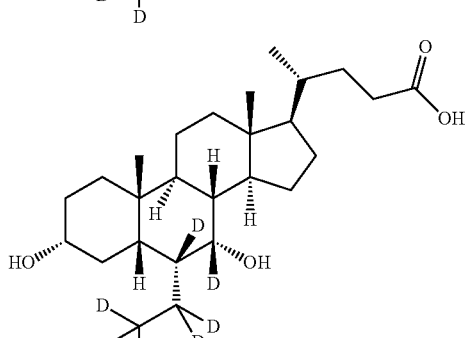
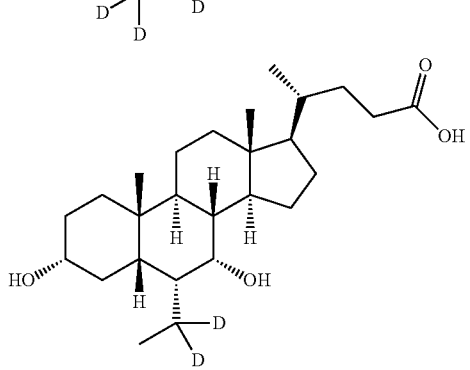

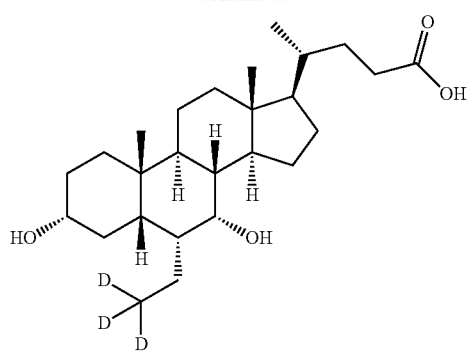
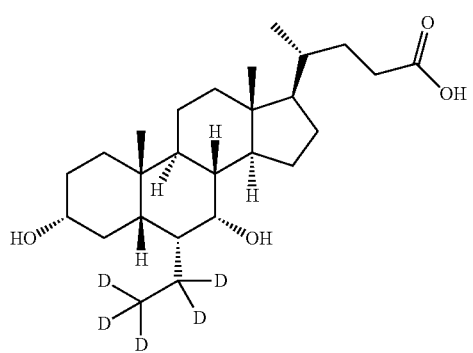
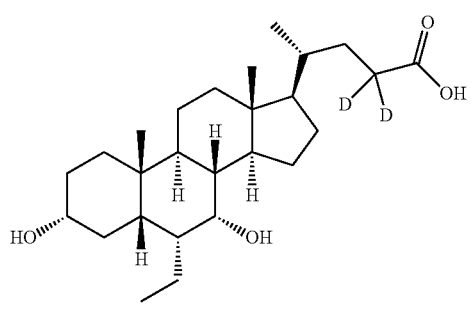
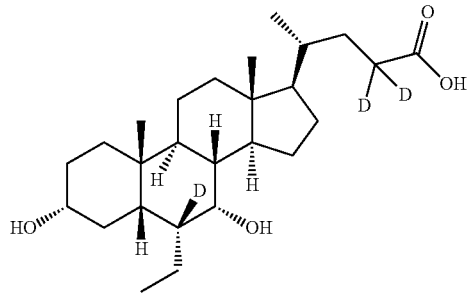
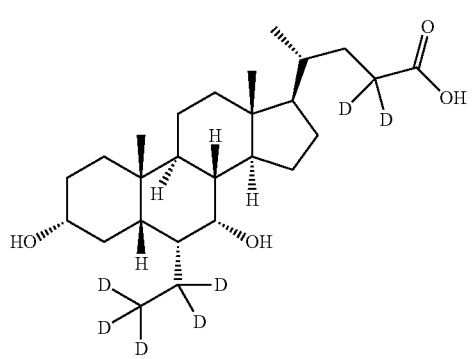
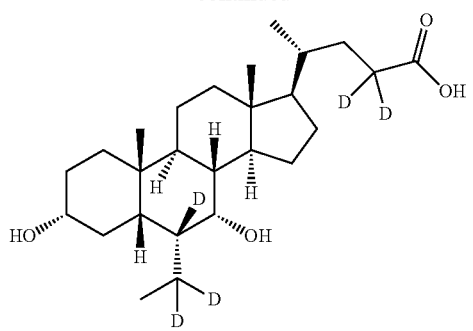
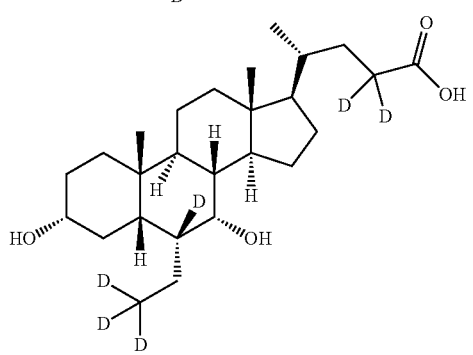
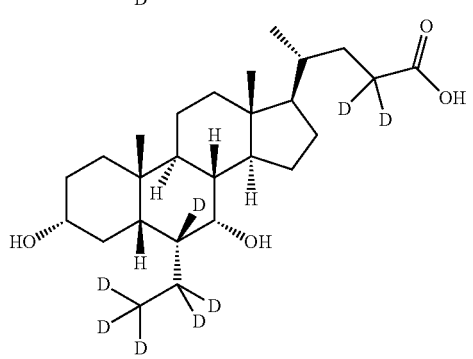
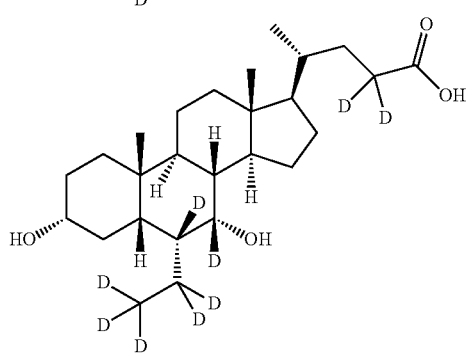
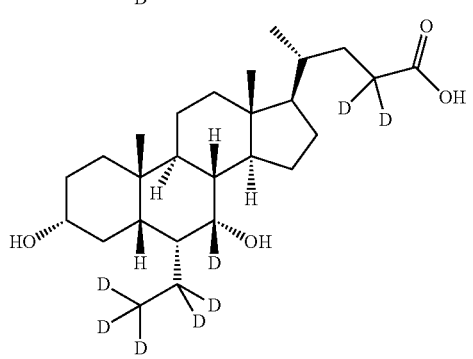

-continued
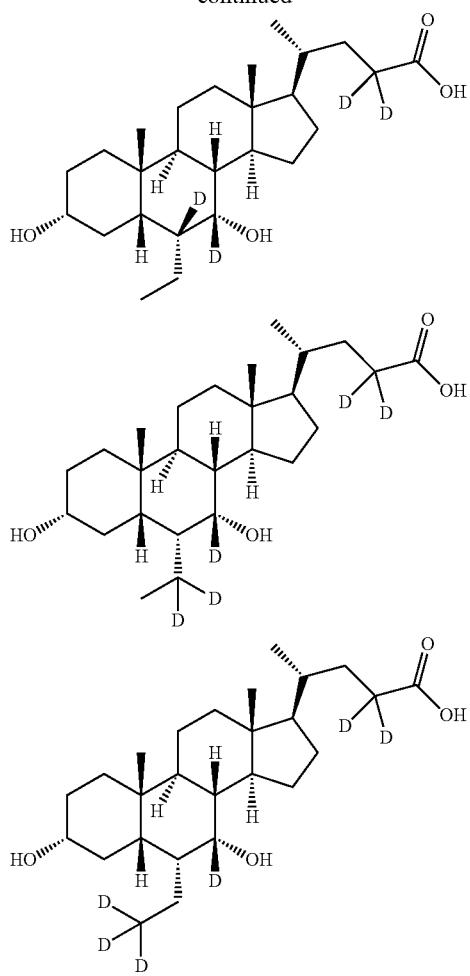
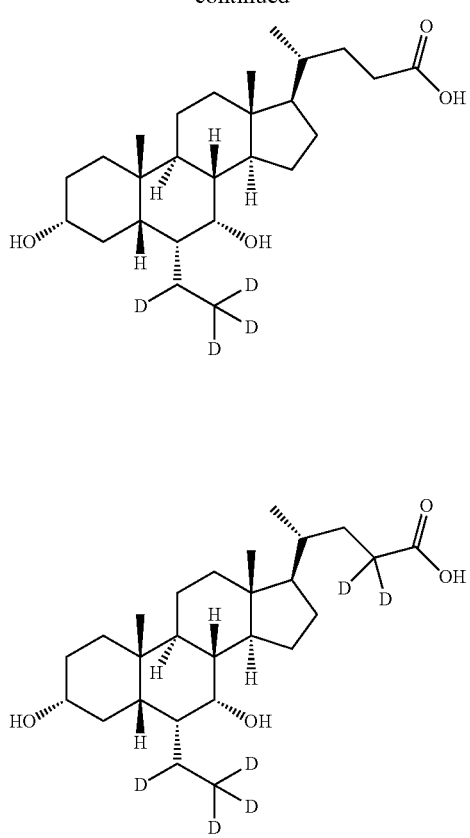
In another preferred embodiment, the compound is one of the following compounds, or the pharmaceutical acceptable salt thereof:
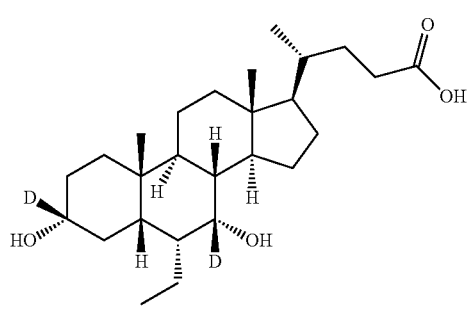
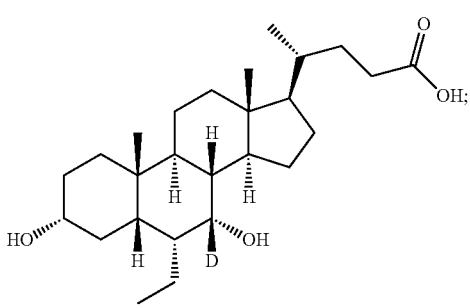
3α, 7α-dihydroxy-6α-ethyl-7-d-5β-cholan-24-oic acid
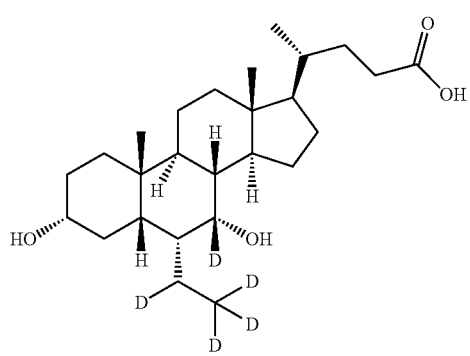
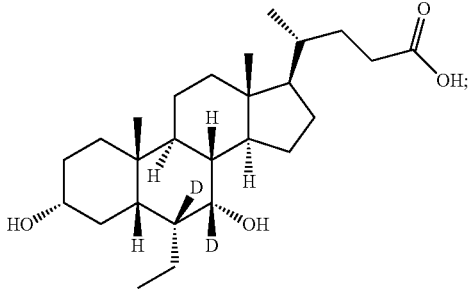
3α, 7α-dihydroxy-6α-ethyl-6, 7-d₂-5β-cholan-24-oic acid

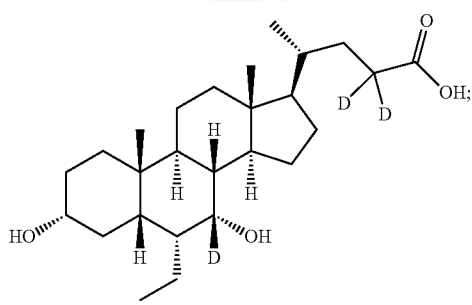
3α,7α-dihydroxy-6α-ethyl-7,23,23-d₃-5β-cholan-24-oic acid
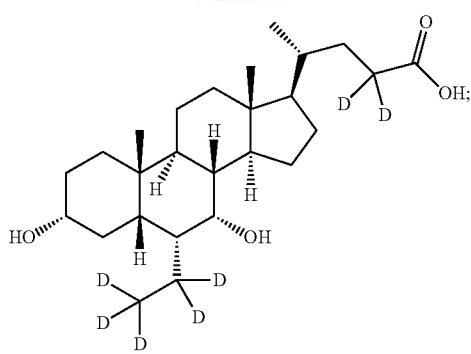
3α,7α-dihydroxy-6α-(ethyl-d₅)-23,23-d₂-5β-cholan-24-oic acid
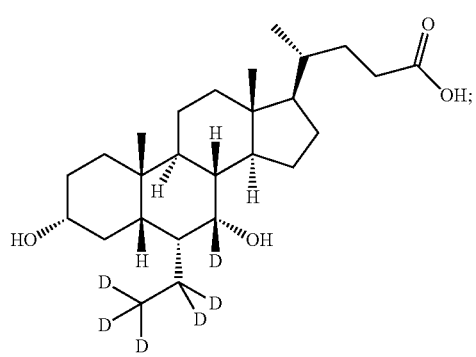
3α,7α-dihydroxy-6α-(ethyl-d₅)-7-d-5β-cholan-24-oic acid
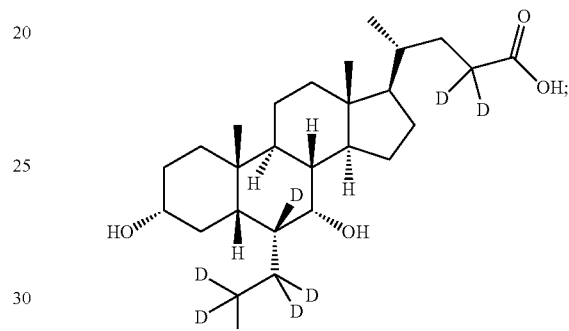
3α,7α-dihydroxy-6α-(ethyl-d₅)-6,23,23-d₂-5β-cholan-24-oic acid
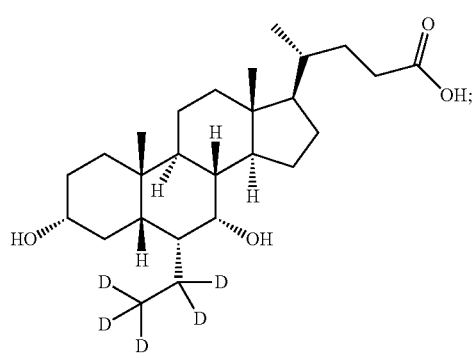
3α,7α-dihydroxy-6α-(ethyl-d₅)-5β-cholan-24-oic acid
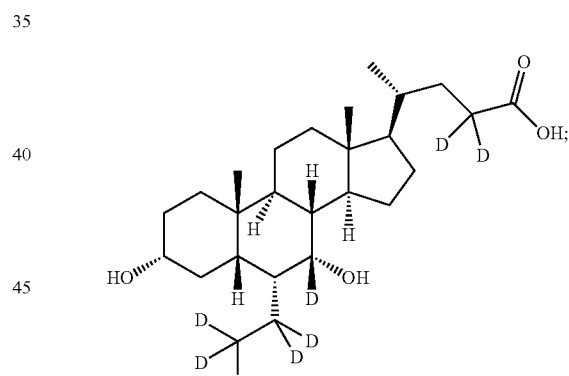
3α,7α-dihydroxy-6α-(ethyl-d₅)-7,23,23-d₃-5β-cholan-24-oic acid
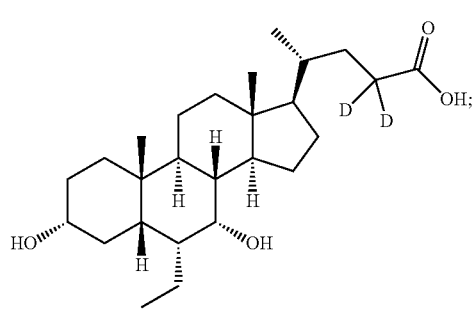
3α,7α-dihydroxy-6α-ethyl-23,23-d₂-5β-cholan-24-oic acid
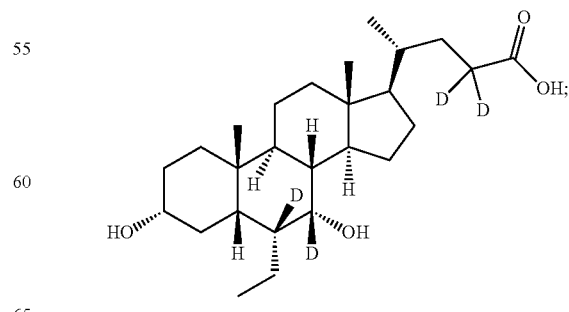
3α,7α-dihydroxy-6α-ethyl-6,7,23,23-d₄-5β-cholan-24-oic acid -continued

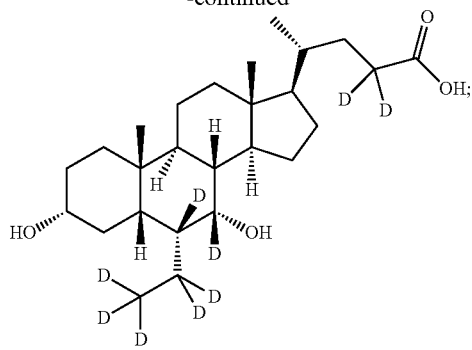

3α, 7α-dihydroxy-6α-(ethyl-d5)-6, 7, 23, 23-d4-5β-cholan-24-oic acid

In another preferred embodiment, the compound is

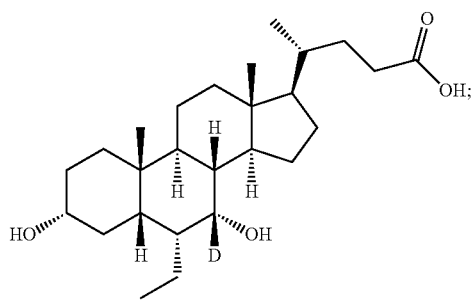

which has the following characteristics: MS calculated value: 421; MS measured value: 422 (M+H)$^+$, 444 (M+Na)$^+$.

In another preferred embodiment, the compound is

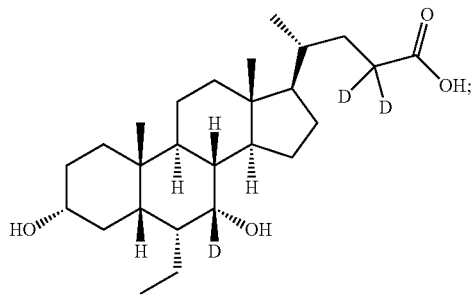

which has the following characteristics: MS calculated value: 423; MS measured value: 424 (M+H)$^+$, 446 (M+Na)$^+$.

In another preferred embodiment, the compound is

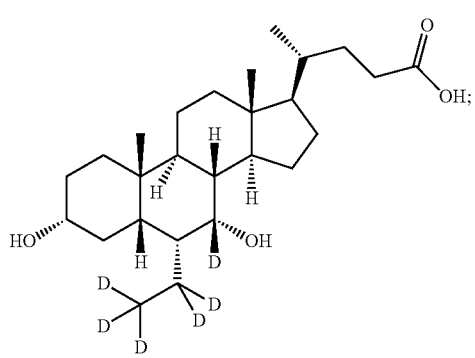

which has the following characteristics: MS calculated value: 426; MS measured value: 427 (M+H)$^+$, 449 (M+Na)$^+$.

In another preferred embodiment, the compound is

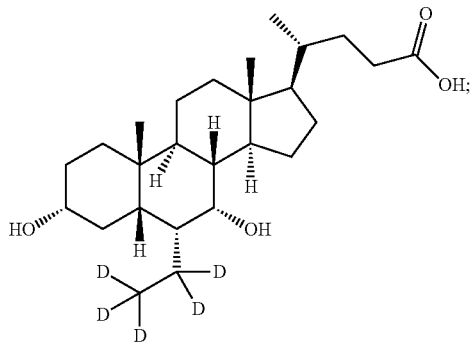

which has the following characteristics: MS calculated value: 425; MS measured value: 426 (M+H)$^+$, 448 (M+Na)$^+$.

In another preferred embodiment, the compound is

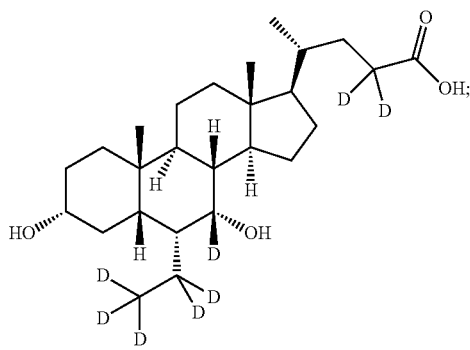

which has the following characteristics: MS calculated value: 428; MS measured value: 429 (M+H)$^+$, 451 (M+Na)$^+$.

In another preferred embodiment, the compound is

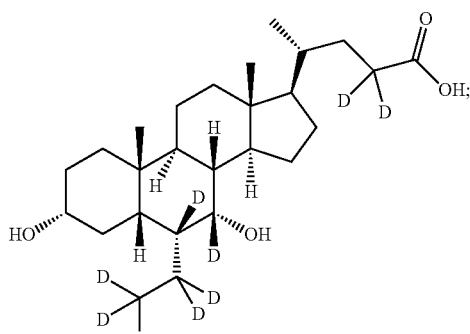

which has the following characteristics: MS calculated value: 429; MS measured value: 430 (M+H)$^+$, 452 (M+Na)$^+$.

In another preferred embodiment, the compound is

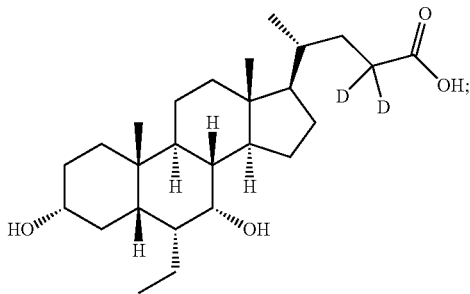

which has the following characteristics: MS calculated value: 422; MS measured value: 423 (M+H)$^+$, 445 (M+Na)$^+$.

In another preferred embodiment, the compound is

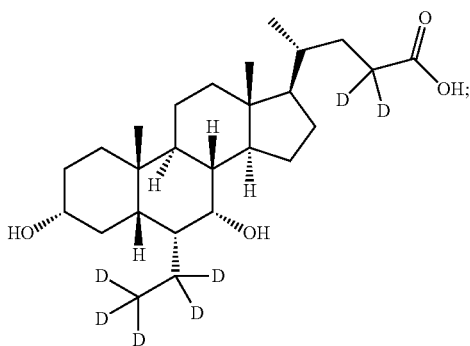

which has the following characteristics: MS calculated value: 427; MS measured value: 428 (M+H)$^+$, 450 (M+Na)$^+$.

In another preferred embodiment, the compound does not comprise any undeuterinated compound.

In another preferred embodiment, the undeuterated compound is oberbinic acid, i.e., 3α,7α-dihydroxy-6α-ethyl-5β-cholan-24-oic acid.

In another preferred embodiment, the compound is prepared by the method described in examples 1-4.

In the second aspect of the present invention, it provides a method for preparing pharmaceutical composition, which comprises the following step: mixing compounds of the first aspect of the present invention, or a crystal form, pharmaceutically acceptable salt, hydrate or solvate thereof and a pharmaceutically acceptable carrier to form a pharmaceutical composition.

In the third aspect of the present invention, it provides a pharmaceutical composition, which comprises pharmaceutically acceptable carrier and the compounds of the first aspect of the present invention, or a crystal form, pharmaceutically acceptable salt, hydrate or solvate thereof.

In another preferred embodiment, the pharmaceutical composition is injections, capsules, tablets, pills, powders or granules.

In another preferred embodiment, the pharmaceutical composition comprises other therapeutic medicine, and the other therapeutic medicine is medicine for the treatment of cancers, cardiovascular diseases, inflammations, infections, immune diseases, metabolic disorders or organ transplantation.

In another preferred embodiment, the cancers include (but are not limited to): lung cancer, breast cancer, prostate cancer, esophageal cancer, rectal cancer, colon cancer, blood cancer (or malignant blood disease), bone cancer, kidney cancer, stomach cancer, liver cancer or colorectal cancer.

In another preferred embodiment, the cancer is liver cancer.

More preferably, the additional therapeutic agent includes (but is not limited to): sorafenib, regorafenib, duonafenib, cisplatin, doxorubicin, gemcitabine, FOLFOX, decitabine, capecitabine, statins (lovastatin, simvastatin, pravastation, mevastatin, fluvastatin, atorvastatin, cerivastatin, rosuvastatin, etc.), rosiglitazone, pioglitazone, metformin, acarbose, voglibose, sulfonylureas (glipizide, gliclazide, glimepiride, etc.), dipeptidyl peptidase-4 (DPP-4) inhibitors hypoglycemic agents (such as sitagliptin, vildagliptin, alogliptin, Trajenta, etc.), sodium-dependent glucose transporters (SGLT2) inhibitor hypoglycemic agents (such as dapagliflozin, canagliflozin, etc.), glucagon-like peptide-1 (GLP-1) receptor agonists ((such as exenatide, liraglutide, lixisenatide, etc.), interferon, pegylated interferon, anti-hepatitis C drugs (such as Sofosbuvir, telaprevir, Boceprevir, ACH-3102, Daclatasvir, Deleobuvir, Ledipasvir, etc.), anti-hepatitis B drugs (such as lamivudine, adefovir dipivoxil, telbivudine, entecavir, tenofovir disoproxil, clevudine, etc.).

In the fourth aspect of the present invention, it provides a use of the compound of the first aspect of the present invention, or the crystal form, pharmaceutically acceptable salt, hydrate or solvate thereof, or the pharmaceutical composition of the third aspect of the present invention in the preparation of pharmaceutical compositions of farnesoid X receptor (FXR) agonist and/or G-protein coupled bile acid receptor (GPBAR or TGR5) agonist.

In another preferred embodiment, it provides the use of pharmaceutical composition in the preparation of drugs for the treatment and prevention of the following diseases: nonalcoholic steatohepatitis, nonalcoholic fatty liver disease, gallstones, primary biliary cirrhosis, cirrhosis, liver fibrosis, diabetes, atherosclerosis, obesity.

In the fifth aspect of the present invention, provided a method for the treatment of farnesoid X receptor (FXR) agonist and/or G-protein coupled bile acid receptor (GPBAR or TGR5) agonist, or a therapeutic method of diseases (such as cancer, nonalcoholic steatohepatitis, nonalcoholic fatty liver disease, gallstones, primary biliary cirrhosis, cirrhosis, liver fibrosis, diabetes, atherosclerosis, obesity), comprising the following steps: administering the compounds of the first aspect of the present invention, or crystal forms, pharmaceutically acceptable salts, hydrates or solvates thereof, or administering the pharmaceutical composition of the third aspect of the present invention to a subject in need.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through research, the inventor has unexpectedly discovered that the deuterated chenodeoxycholic acid derivative or the pharmaceutically acceptable salts thereof are obviously superior to the undeuterated compound in pharmacokinetic and/or pharmacodynamic properties, therefore more suitable for the use as farnesoid X receptor (FXR) agonist and/or G-protein coupled bile acid receptor (GPBAR or TGR5) agonist compounds, further, more suitable to use in the preparation of the medicines for treatment of cancer and diseases for the treatment of diseases associated to farnesoid X receptor (FXR) and/or G-protein coupled bile acid receptor (GPBAR or TGR5). The present invention is completed on this basis.

Definitions

As used herein, term "halogen" refers to F, Cl, Br and I. More preferably, the halogen atom is selected from F, Cl and Br.

As used herein, "superior pharmacokinetic and/or pharmacodynamic properties" refers to a longer half-life drugs ($t_{1/2}$), or a higher drug exposure (AUC), or higher maximum drug concentration ($C_{max}$), or lower drug clearance rate.

As used herein, "deuterated" means one or more hydrogen in a compound or group is replaced by deuterium.

As used herein, "undeuterated compound" means a compound containing a deuterium atom ratio that is not higher than the natural deuterium isotope content (0.015%).

In another preferred embodiment, deuterium isotope content of the deuterium substituted position is greater than the natural isotopic deuterium content (0.015%), more preferably greater than 50%, more preferably greater than 75%, more preferably greater than 95%, more preferably greater than 97%, more preferably greater than 99%, more preferably greater than 99.5%.

In another preferred embodiment, the compound of formula (I) contains at least one deuterium atom, more preferably two deuterium atoms, three deuterium atoms, more preferably four deuterium atoms, more preferably six deuterium atoms.

Preferably, in the compound of formula (I), O is $^{16}$O.

In another preferred embodiment, in the compound, the $^{16}$O isotope content in the oxygen atom position is ≥95%, preferably ≥99%.

Active Ingredients

As used herein, the term "compound of the invention" refers to formula (I) compound. The term also comprises the crystal forms, pharmaceutically acceptable salts, hydrates or solvates of compound of formula (I).

As used herein, the term "pharmaceutically acceptable salts" refers to salts suitable for use in pharmaceutical which is formed by compound of the present invention with an acid or base. The pharmaceutically acceptable salts include inorganic and organic salts. Preferred type of salts is salts formed by the compounds of the present invention and acid. Acids suitable for forming salts include, but are not limited to, amino acids such as proline, phenylalanine, aspartic acid, glutamic acid and the like. Another preferred type of salts are salts formed by compounds of the present invention and bases, e.g., alkali metal salts (e.g. sodium or potassium salts), alkaline earth metal salts (e.g. calcium or magnesium salts), ammonium salts (e.g., lower alkanol ammonium salts or other pharmaceutically acceptable amine salts), for example, methylamine salt, ethylamine salt, propylamine salt, dimethylamine salt, trimethylamine salts, diethylamine salts, triethylamine salts, tert-butyl amine salts, ethylenediamine salts, hydroxyethylamine salts, bi-hydroxyethylamine salts, tri-hydroxyethylamine salts, and amine salts formed by morpholine, piperazine, and lysine.

The term "solvate" means a compound of the present invention and solvent molecules form a complex specific ratio. "Hydrate" means a compound of the present invention with water to form a coordination complex.

Furthermore, the compounds of the present invention further comprise chiral enantiomers, or racemates of chenodeoxycholic acid derivative of formula (I).

In addition, the compounds of the present invention further include glucuronide conjugates (glucuronides) and taurine conjugates of the chenodeoxycholic acid derivative of the formula (I).

In addition, the compounds of the present invention further include prodrugs of the chenodeoxycholic acid derivative of formula (I). The term "prodrug" includes itself may be a biologically active or inactive, when administered by an appropriate method, for which metabolic or chemical reactions in the human body and converted into a class of compounds of formula (I) or a salt or solution of a compound of formula (I). The prodrugs include, but are not limited to, carboxylic acid esters, carbonate esters, phosphate esters, nitric acid esters, sulfuric esters, sulfone esters, sulfoxide ester, amino compounds, carbamates, azo compounds, phosphoramides, glucosides, ethers, acetals and the like.

Preparation Method

Hereinafter more specifically describes the preparation of compounds of formula (I), but such specific methods do not constitute any limitation to the present invention. The compounds of the invention may also be easily prepared by optionally combine various synthetic methods described in this specification or known in the art, such a combination can be easily performed by one of ordinary skill in the art of the present invention.

The methods of preparing the undeuterated chenodeoxycholic acid derivative and physiologically compatible salts thereof used in the present invention are known. Preparation of corresponding deuterated chenodeoxycholic acid derivative can be conducted by using the corresponding deuterated starting compound, and synthesizing by the same route. For example, a compound of formula (I) of the present invention can be prepared according to the method described in WO02072598, except that the deuterated material is used instead of the undeuterated material.

Generally, in the preparation process, each reaction is generally conducted in an inert solvent, under room temperature to reflux temperature (such as 0° C.-200° C., preferably from 0° C.-100° C.). The reaction time is usually 0.1 hours-60 hours, preferably 0.5 to 48 hours.

The following general preparative route 1 and 2 may be used in the synthesis of compounds of formula (I) of the present invention.

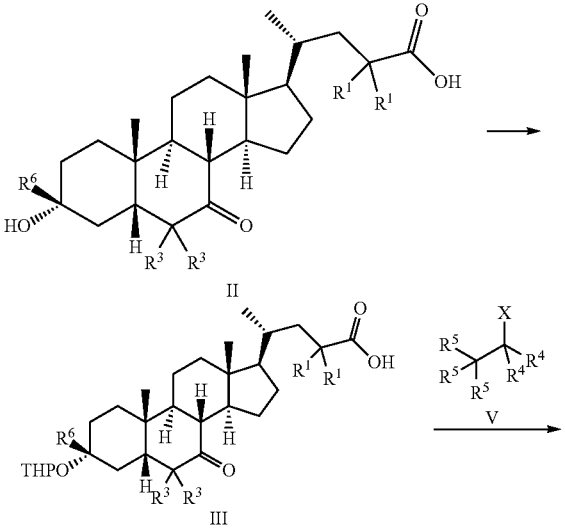

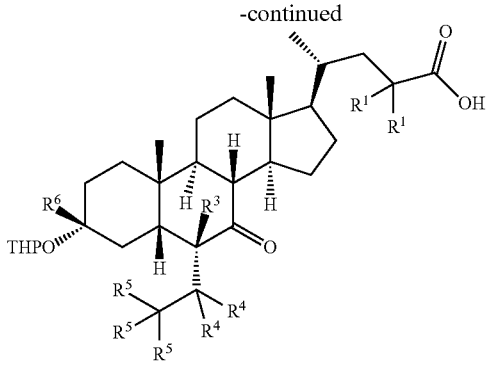

IV

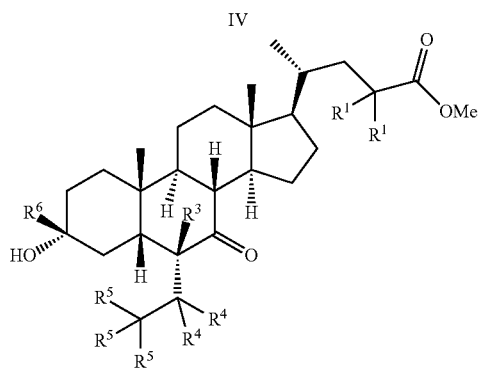

VI

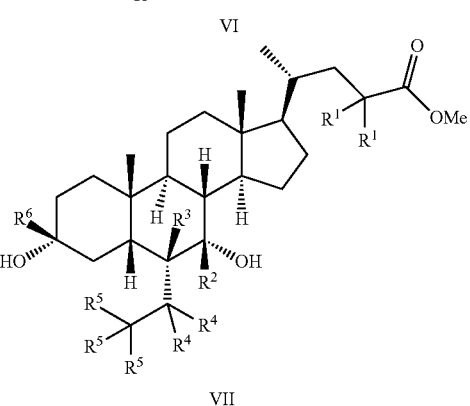

VII

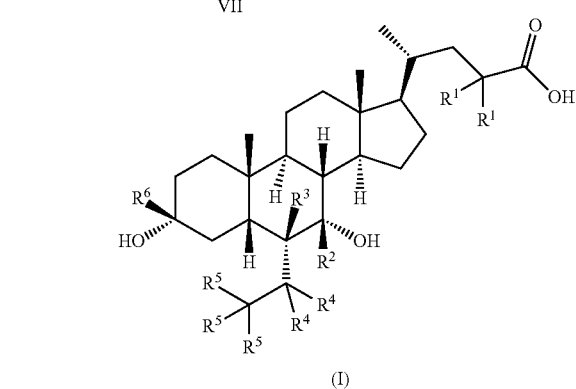

(I)

Synthetic Route 1

Wherein $R^1$, $R^2$, $R^3$, $R^4$, $R^5$ and $R^6$ are as defined above and X is halogen.

As shown in synthetic route 1, compound III is obtained by protecting the hydroxyl of compound II by THP. Compound III and Compound V undergo a substitution reaction to give compound IV under the action of alkali. Compound IV is deprotected and esterified in acid and methanol to give compound VI. Compound VI was reduced to give compound VII. Finally compound VII of the present invention is obtained by hydrolysis of compound VII. The above reaction is carried out in an inert solvent such as dichloromethane, acetonitrile, n-hexane, toluene, tetrahydrofuran, N,N-dimethylformamide, N,N-dimethylacetamide, dimethylsulfoxide, acetic acid, butanol, propanol and the like, at a temperature of 0 to 200° C.

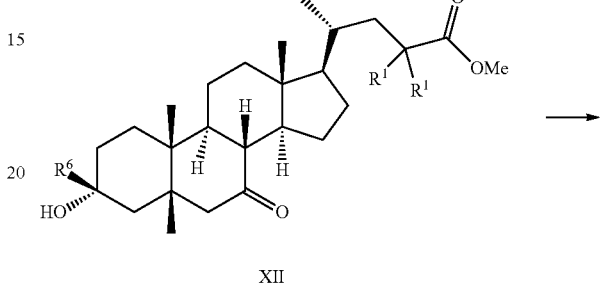

XII

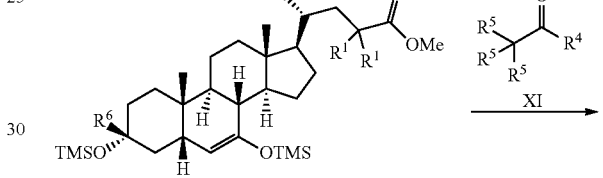

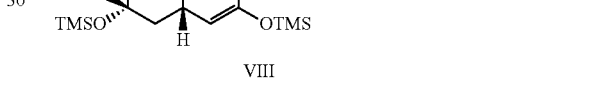

VIII

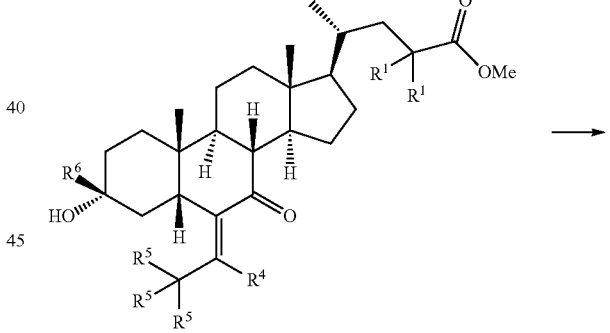

IX

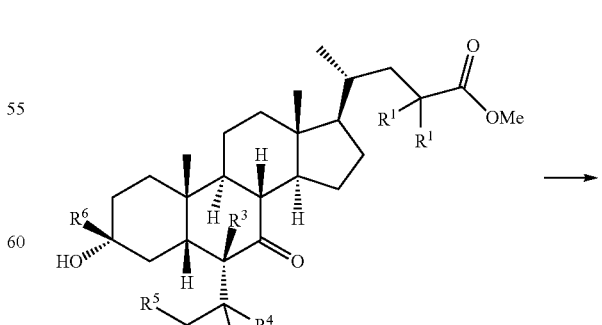

VI

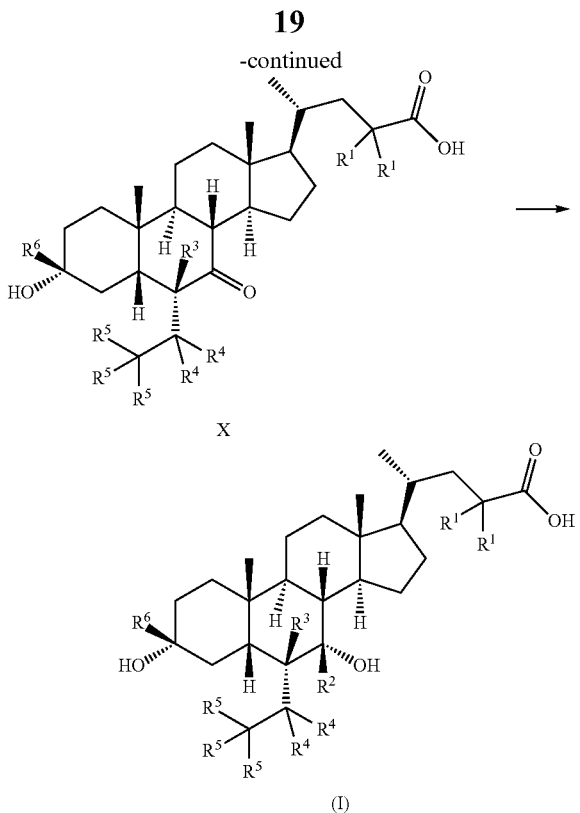

Synthetic Route 2

As shown in Synthetic route 2, compound VIII is obtained by protecting hydroxyl of methyl ester compound XII with TMS. Compound IX is obtained via aldol condensation and elimination reaction of compound VIII and aldehyde compound XI. Compound IX was reduced to give compound VI; compound VI was hydrolyzed to give compound X, and finally compound X was reduced to give compound I.

The above reaction is carried out in an inert solvent such as dichloromethane, acetonitrile, n-hexane, toluene, tetrahydrofuran, N, N-dimethylformamide, N, N-dimethylacetamide, dimethylsulfoxide, acetic acid, butanol, propanol and the like at a temperature of −100° C. to 200° C.

Pharmaceutical Composition and the Administration Thereof

The compounds of the present invention possess outstanding activation activity of farnesoid X receptor (FXR) and/or G-protein conjugated cholic acid receptor (GPBAR or TGR5). Therefore, the compound of the present invention, and the crystal forms, pharmaceutically acceptable inorganic or organic salts, hydrates or solvates thereof, and the pharmaceutical composition comprising the compound of the present invention as a main active ingredient can be used for treating, preventing and alleviating diseases mediated by farnesoid X receptor (FXR) and/or G-protein conjugated cholic acid receptor (GPBAR or TGR5). According to the prior art, the compounds of the present invention are useful in the treatment of the following diseases: cancers, nonalcoholic steatohepatitis, nonalcoholic fatty liver disease, gallstones, primary biliary cirrhosis, cirrhosis, liver fibrosis, diabetes, atherosclerosis, obesity, etc.

The pharmaceutical composition of the invention comprises the compound of the present invention or the pharmaceutically acceptable salts thereof in a safe and effective dosage range and pharmaceutically acceptable excipients or carriers. The "safe and effective amount" means: the amount of the compound sufficient to significantly improve the condition, but will not have serious side effects. Generally, the pharmaceutical composition contains 0.5-2000 mg crystal forms of the invention per dose, preferably, 1-500 mg crystal forms of the invention per dose, preferably, "one dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatible" herein means that each component in the composition and a compound of the present invention can be well blended with each other between them, without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, duodenum, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants.

The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 0.5-2000 mg, preferably 1-500 mg.

Of course, the particular dose should also depend on various factors, such as the route of administration, patient healthy status, which are well within the skills of an experienced physician.

Compared to the prior art known undeuterated compounds, the compounds of the present invention possess a number of advantages. The main advantages of the present invention are:

(1) The compounds of the present invention have excellent activating activity against farnesoid X receptor (FXR) and/or G-protein coupled bile acid receptor (GPBAR or TGR5).

(2) The metabolism of the deuterated compounds in the organism is changed by deuterate technology, thus making the compound of better pharmacokinetic parameters characteristic. In this case, the dose may be varied and form a long-acting preparation to improve the applicability.

(3) The hydrogen in the compounds has been substituted with deuterium, the drug concentration of the compound in animals can be enhanced by the deuterium isotope effect, thus improving drug efficacy.

(4) The hydrogen in the compounds has been substituted with deuterium, since some metabolites is suppressed, the safety of compound may be improved.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1 Synthesis of 3α, 7α-Dihydroxy-6α-Ethyl-7-d-5β-Cholan-24-Oic Acid (Compound 1)

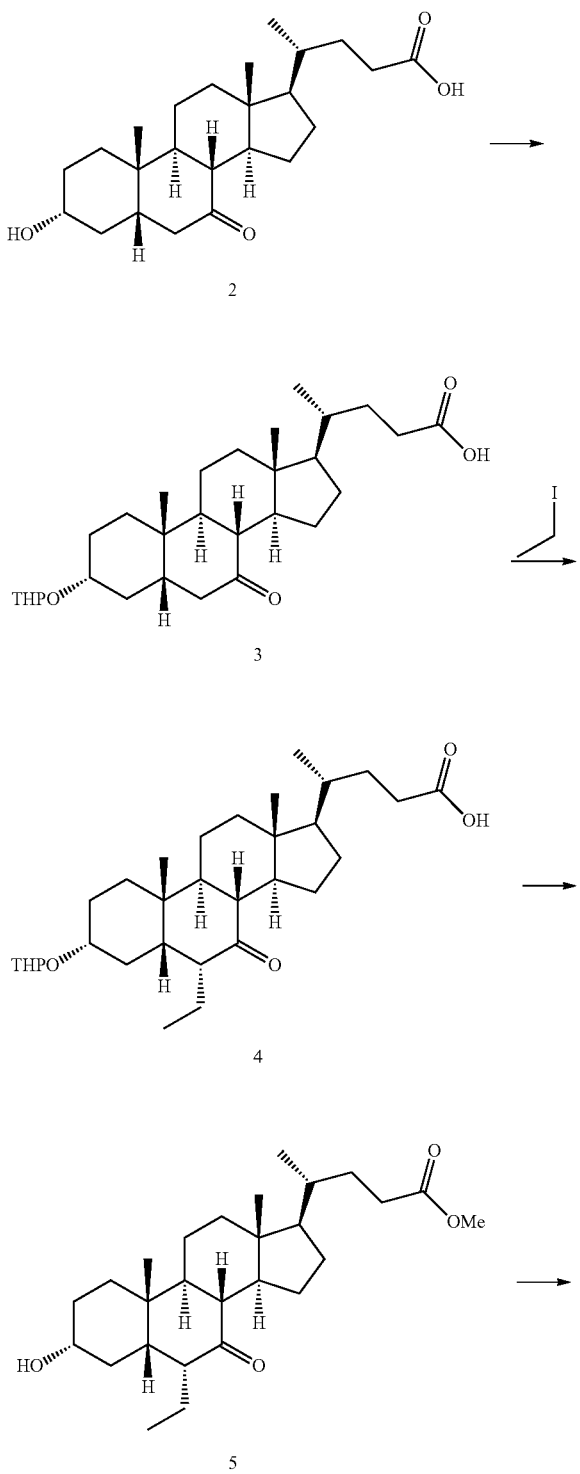

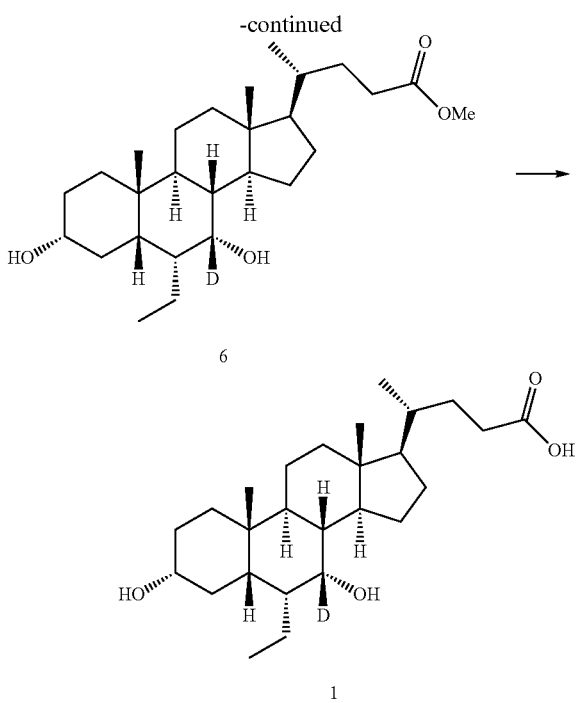

1. Synthesis of 3α-tetrahydropyranyloxy-7-keto-5β-cholan-24-oic Acid (Compound 3)

3α-hydroxy-7-keto-5β-cholan-24-oic acid (10.0 g, 25.6 mmol) was dissolved in dioxane (150 ml) in a flask. p-Toluenesulfonic acid monohydrate (0.49 g, 2.56 mmol) and 3,4-dihydro-2H-pyran (4.31 g, 51.2 mmol) were added in turn. After stirring at room temperature for 1 h, ammonia solution in methanol was dropwisely added to adjust pH to 8-9. After the volatiles were removed by evaporation, the residue was extracted with EtOAc. The organic phase was washed subsequently with sat. sodium bicarbonate, water and saturated brine, and dried with Na$_2$SO$_4$. After filtration, the filtrate was condensed with the rotary evaporator. The resulting crude product was purified by silica gel column chromatograph (EtOAc/petroleum=1/3) to get the off-white solid target compound (9.72 g, 80%).

2. Synthesis of 3α-tetrahydropyranyloxy-6α-ethyl-7-keto-5β-cholan-24-oic Acid (Compound 4)

Diisopropylamine (5.8 g, 57.6 mmol) in dry THF (400 ml) was added into the flask and cooled to −78° C. Under −60° C., n-butyllithium (23.1 ml, 2.5M in hexane) and hexamethylphosphoric triamide (HMPA, 10.3 g, 57.6 mmol) was added drop-wise in turn. After stirring for 1 h at −70° C., added drop-wise to the pre-cooled (−78° C.) solution of 3α-tetrahydropyranyloxy-7-keto-5β-cholan-24-oic (compound 3, 9.1 g, 19.2 mmol) in dry THF (200 ml), then stirred for another 30 min. Iodoethane (29.9 g, 192 mmol) in dry THF (1000 ml) was then slowly added and the reaction mixture, and was stirred at room temperature overnight. After the volatiles were removed under vacuum, the residue was adjusted to pH 2-3 with 10% HCl, and extracted with EtOAc. The combined organic fraction was washed subsequently with 5% sodium hyposulfite, water and brine, dried with Na$_2$SO$_4$ and filtered. The filtrate was evaporated to get the target product, which was used directly in the next step without further purification.

3. Synthesis of Methyl 3α-hydroxy-6α-ethyl-7-keto-5β-cholan-24-oate (Compound 5)

Crude compound 3α-tetrahydropyranyloxy-6α-ethyl-7-keto-5β-cholan-24-oic acid obtained in the previous step was dissolved in HCl solution in methanol (2N, 120 ml) and stirred under reflux for 16 h. After the volatiles were removed under vacuum, the residue was extracted with EtOAc. The combined organic fraction was washed subsequently with water, sat. NaHCO$_3$ solution and brine, dried with Na$_2$SO$_4$ and filtered. After the filtrate was evaporated, the residue was purified by silica gel column chromatography (20-40% EtOAc/hexane) to afford the target compound 5 (1.8 g, yield 21.7% from compound 3).

4. Synthesis of Methyl 3α,7α-dihydroxy-6α-ethyl-7-d-5β-cholan-24-oate (Compound 6)

Methyl 3α-hydroxy-6α-ethyl-7-keto-5β-cholan-24-oate (1.5 g, 3.5 mmol) was dissolved in methanol (6 ml) in a flask and stirred. Sodium borodeuteride (NaBD$_4$, 0.3 g, 7 mmol, Sigma-Aldrich) was added and the mixture was stirred for another 3 h at room temperature. Water was added to quench the reaction. The mixture was concentrated under high vacuum and extracted with EtOAc. The combined organic fraction was washed subsequently with water and brine, dried with Na$_2$SO$_4$ and filtered. The filtrate was evaporated to afford the target compound (1.3 g, 85%).

5. Synthesis of 3α, 7α-dihydroxy-6α-ethyl-7-d-5β-cholan-24-oic Acid (Compound 1)

To a flask was added methyl 3α,7α-dihydroxy-6α-ethyl-7-d-5β-cholan-24-oate (1.2 g, 2.8 mmol), sodium hydroxide solution in water (10%, 2.24 g, 5.6 mmol), and THF/MeOH/water mixture solution (1/3/2, 20 ml). The mixture was stirred at 40° C. for 6 h. 3N HCl was added to adjust pH to 2-3. The mixture was extracted with EtOAc. The combined organic fraction was washed subsequently with water and brine, dried with Na$_2$SO$_4$ and filtered. The filtrate was concentrated and the residue was purified by silica gel chromatography (5% methanol/dichloromethane) to afford the target compound (0.87 g, 75%). $^1$H NMR (400 MHz, CDCl$_3$+CD$_3$OD) δ: 3.46 (m, 1H), 2.35-0.74 (m, 27H), 0.95 (d, 3H), 0.89-0.92 (m, 6H), 0.68 (s, 3H). ESI-MS (m/z): 422 (M+H)$^+$, 444 (M+Na)$^+$.

The Alternative Scheme to Prepare Compound 1

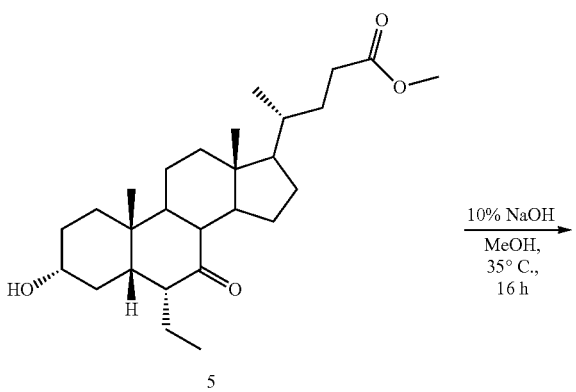

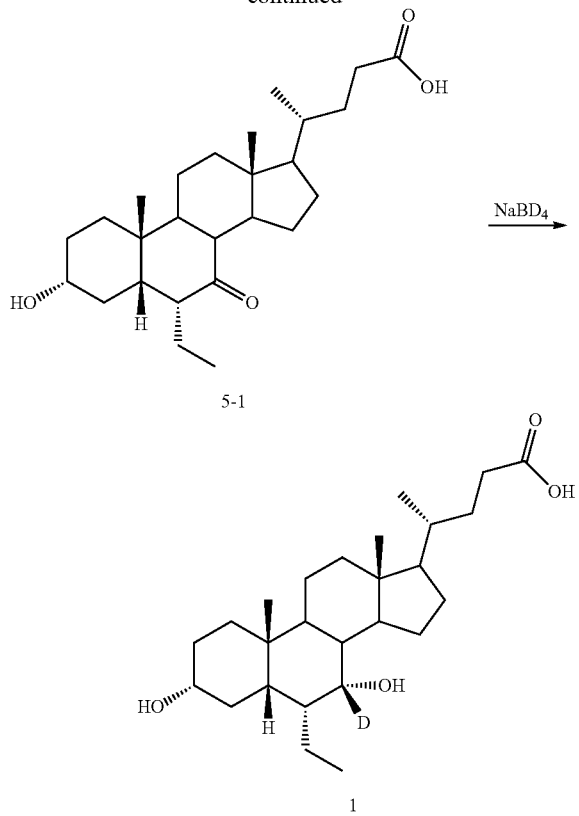

5-1

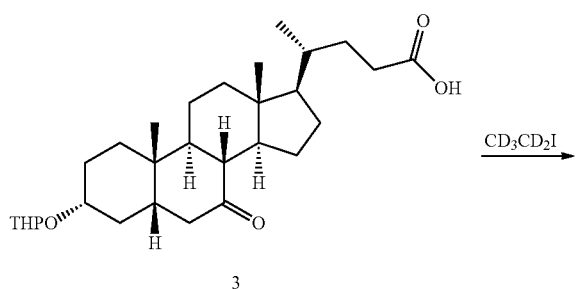

1

To a flask was subsequently added Methyl 3α-hydroxy-6α-ethyl-7-keto-5β-cholan-24-oate (2.0 g, 4.6 mmol), sodium hydroxide solution in water (10%, 4.0 ml) and methanol/water mixture solution (3/1, 20 ml). The mixture was stirred at 35° C. for 16 h. After concentration, the residue was added with water (10 ml), adjusted pH to 2-3 with 1N HCl. The precipitate was filtrated and washed with purified water followed by drying to afford compound 5-1 (1.7 g, 88%).

Compound 5-1 (1.0 g, 2.4 mmol), sodium hydroxide solution (50%, 0.5 ml) and water (8.0 ml) was added a flask. Sodium borodeuteride (103 mg, 2.4 mmol) was added by portion-wise and the mixture was stirred at 100° C. overnight. The mixture was cooled to room temperature and added 1N HCl to adjust pH 2-3. The precipitate was filtrated, washed with water and dried to afford the target compound (520 mg, 51%). NMR (400 MHz, DMSO-$d_6$) δ: 11.95 (brs, 1H), 4.23-4.01 (m, 2H), 3.16-3.11 (m, 1H), 2.28-2.20 (m, 1H), 2.15-2.07 (m, 1H), 1.93-0.83 (m, 34H), 0.61 (s, 3H).

Example 2 Synthesis of 3α, 7α-Dihydroxy-6α-(Ethyl-$d_5$)-7-d-5β-Cholan-24-Oic Acid (Compound 10)

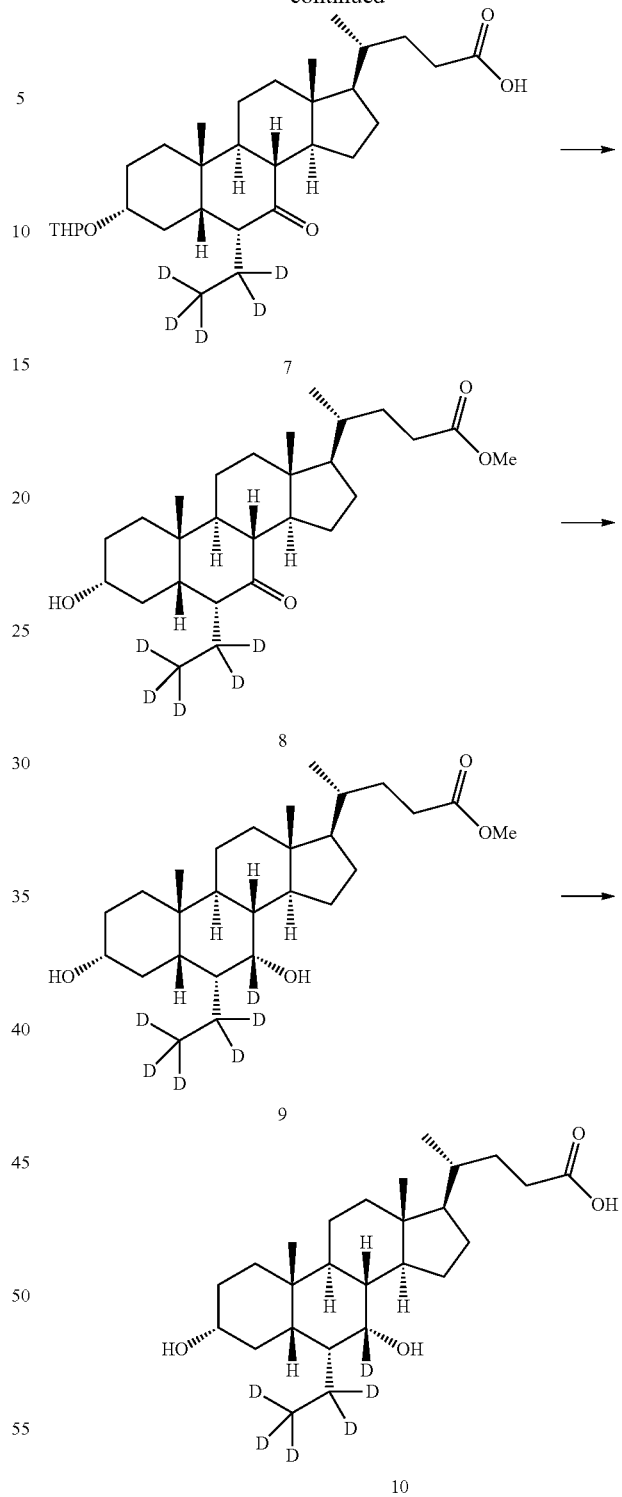

1. Synthesis of 3α-tetrahydropyranyloxy-6α-(ethyl-$d_5$)-7-keto-5β-cholan-24-oic Acid (Compound 7)

Diisopropylamine (2.3 g, 23 mmol) in dry THF (200 ml) was added into flask and cooled to −78° C. The temperature was kept under −60° C., n-butyllithium (9.2 ml, 2.5M in hexane) and hexamethylphosphoric triamide (HMPA, 4.2 g, 23 mmol) was subsequently added drop-wise. After addition, the mixture was stirred for 1 h at −70° C. The pre-cooled (−78° C.) solution of 3α-tetrahydropyranyloxy-7-keto-5β-cholan-24-oic (Compound 3, 3.6 g, 7.6 mmol) in dry THF (100 ml) was added drop-wise. After stirring for another 30 min, iodoethane-d5 (6.2 g, 38 mmol) in dry THF (200 ml) was slowly added drop-wise and the mixture was stirred at room temperature overnight. After the volatiles were removed by concentration under vacuum, the residue was adjusted to pH 2-3 with 10% HCl, and extracted with EtOAc. The combined organic fraction was washed subsequently with 5% sodium hyposulfite, water and brine, dried with $Na_2SO_4$ and concentrated to obtain the target product, which was directly used in the next step without further purification.

2. Synthesis of Methyl 3α-hydroxy-6α-(ethyl-$d_5$)-7-keto-5β-cholan-24-oate (Compound 8)

3α-tetrahydropyranyloxy-6α-(ethyl-$d_5$)-7-keto-5β-cholan-24-oic acid obtained in the previous step was dissolved in HCl solution in methanol (2N, 30 ml) and stirred under reflux for 16 h. After the volatiles were removed by concentration under vacuum, the residue was extracted with EtOAc. The combined organic fraction was washed subsequently with water, sat. $NaHCO_3$ solution and brine, dried with $Na_2SO_4$ and concentrated, and the residue was purified by silica gel column chromatography (20-40% EtOAc/hexane) to afford a solid (0.6 g, yield 18%).

3. Synthesis of Methyl 3α, 7α-dihydroxy-6α-(ethyl-$d_5$)-7-d-5β-cholan-24-oate (Compound 9)

Methyl 3α-hydroxy-6α-(ethyl-$d_5$)-7-keto-5β-cholan-24-oate (0.3 g, 0.68 mmol) dissolved in methanol (3 ml) was added into the flask and stirred. Sodium borodeuteride (60 mg, 1.4 mmol) was added and the mixture was stirred for another 3 h at room temperature. Water was added to quench the reaction. The mixture was concentrated under high vacuum and extracted with EtOAc. The combined organic fraction was washed subsequently with water and brine, dried with $Na_2SO_4$ and filtered. The filtrate was concentrated to afford the target compound as a white solid (0.25 g, 82%).

4. Synthesis of 3α, 7α-dihydroxy-6α-(ethyl-$d_5$)-7-d-5β-cholan-24-oic Acid (Compound 10)

To the flask was subsequently added methyl 3α,7α-dihydroxy-6α-(ethyl-$d_5$)-7-d-5β-cholan-24-oate (0.24 g, 0.54 mmol), sodium hydroxide solution (10%, 0.44 g, 1.1 mmol) and THF/MeOH/water mixture (1/3/2, 5 ml). The mixture was stirred at 40° C. for 6 h. 3N HCl solution was added to adjust pH to 2-3, then extracted with EtOAc. The combined organic fraction was washed subsequently with water and brine, dried with $Na_2SO_4$, filtered and concentrated to obtain the solid crude product, purified by silica gel chromatography (5% methanol/dichloromethane) to afford the target compound (0.18 g, 78%). $^1$H NMR (400 MHz, $CDCl_3$+$CD_3OD$) δ: 3.47 (m, 1H), 2.36-0.74 (m, 25H), 0.95 (d, 3H), 0.91 (s, 3H), 0.66 (s, 3H). ESI-MS (m/z): 427 $(M+H)^+$, 449 $(M+Na)^+$.

Example 3 Synthesis of 3α, 7α-Dihydroxy-6α-(Ethyl-$d_5$)-5β-Cholan-24-Oic Acid (Compound 12)

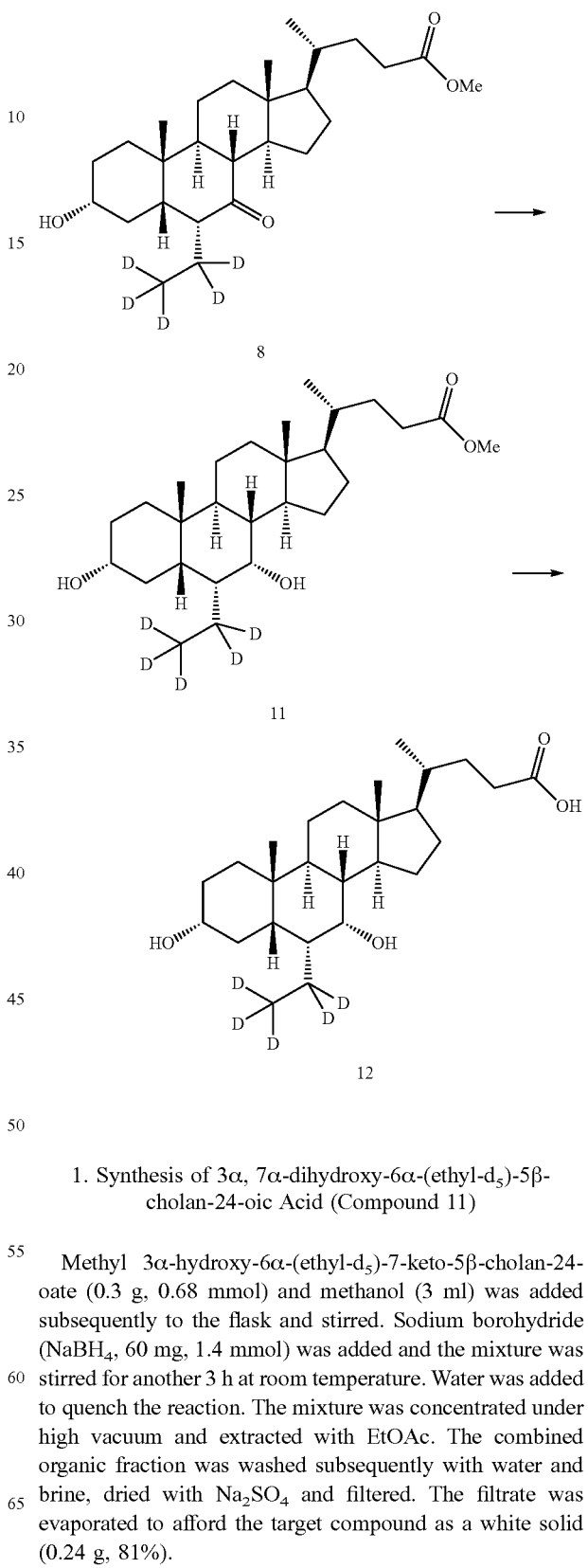

1. Synthesis of 3α, 7α-dihydroxy-6α-(ethyl-$d_5$)-5β-cholan-24-oic Acid (Compound 11)

Methyl 3α-hydroxy-6α-(ethyl-$d_5$)-7-keto-5β-cholan-24-oate (0.3 g, 0.68 mmol) and methanol (3 ml) was added subsequently to the flask and stirred. Sodium borohydride ($NaBH_4$, 60 mg, 1.4 mmol) was added and the mixture was stirred for another 3 h at room temperature. Water was added to quench the reaction. The mixture was concentrated under high vacuum and extracted with EtOAc. The combined organic fraction was washed subsequently with water and brine, dried with $Na_2SO_4$ and filtered. The filtrate was evaporated to afford the target compound as a white solid (0.24 g, 81%).

2. Synthesis of 3α, 7α-dihydroxy-6α-(ethyl-d₅)-5β-cholan-24-oic Acid (Compound 12)

To a flask was subsequently added 3α, 7α-dihydroxy-6α-(ethyl-d₅)-5β-cholan-24-oic acid (0.24 g, 0.54 mmol), sodium hydroxide solution (10%, 0.44 g, 1.1 mmol) and THF/MeOH/water mixture (1/3/2, 5 ml). The mixture was stirred at 40° C. for 6 h. 3N HCl aq. solution was added to adjust pH 2-3. The mixture was extracted with EtOAc. The combined organic fraction was washed subsequently with water and brine, dried with Na₂SO₄ and filtered. The filtrate was concentrated to obtain crude product, which was purified by silica gel column chromatography (5% methanol/dichloromethane) to afford the target compound (0.16 g, 72%). ¹H NMR (400 MHz, DMSO-d₆) δ: 11.97 (brs, 1H), 4.32 (d, J=4.0 Hz, 1H), 4.07 (d, J=4.0 Hz, 1H), 3.50 (s, 1H), 3.14-3.13 (m, 1H), 2.27-2.20 (m, 1H), 2.15-2.07 (m, 1H), 1.93-0.84 (m, 29H), 0.61 (s, 3H). ESI-MS (m/z): 426 (M+H)⁺, 448 (M+Na)⁺.

Example 4 Synthesis of 3α, 7α-Dihydroxy-6α-(Ethyl-d₃)-7-d-5β-Cholan-24-Oic Acid (Compound 18)

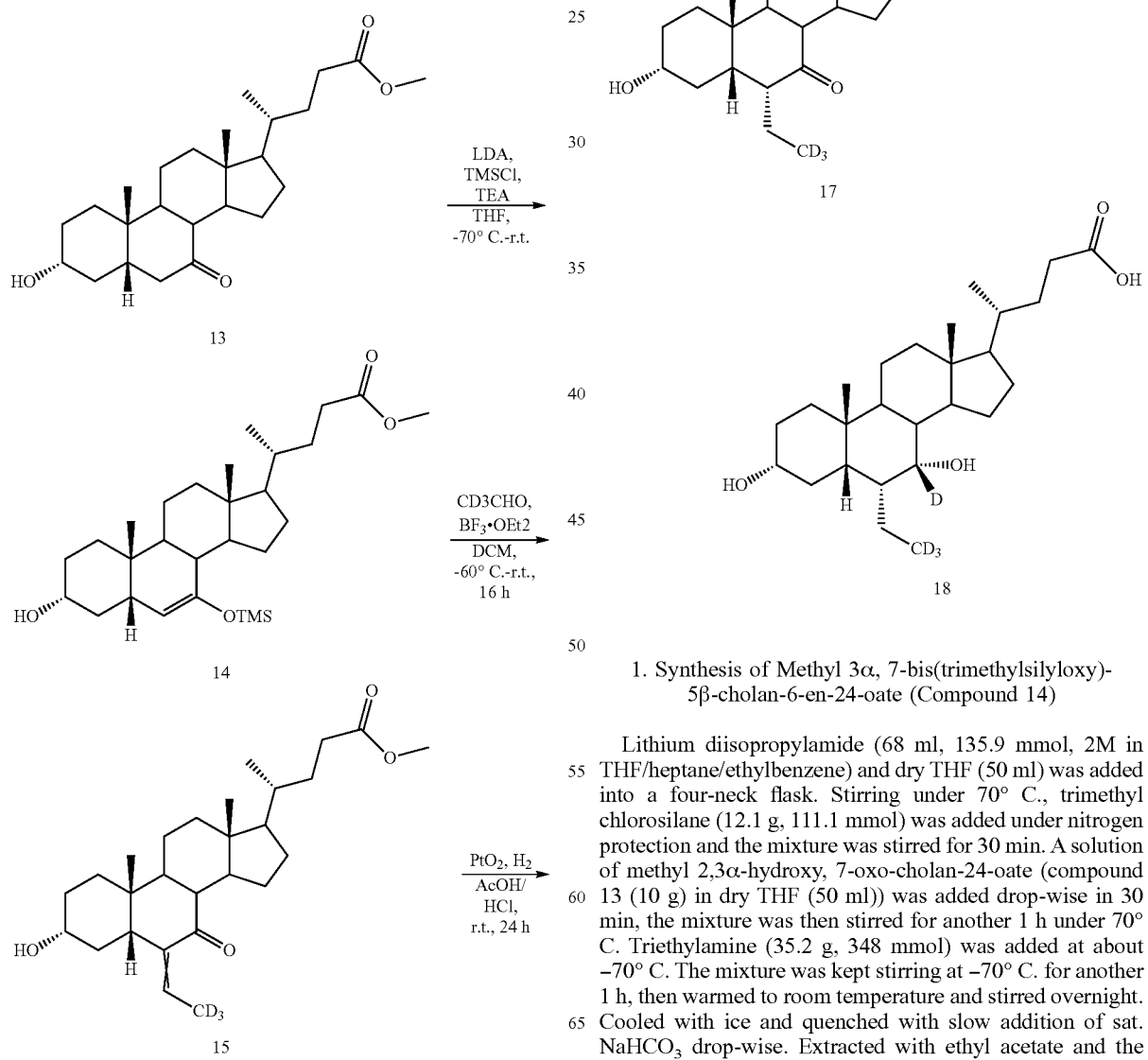

1. Synthesis of Methyl 3α, 7-bis(trimethylsilyloxy)-5β-cholan-6-en-24-oate (Compound 14)

Lithium diisopropylamide (68 ml, 135.9 mmol, 2M in THF/heptane/ethylbenzene) and dry THF (50 ml) was added into a four-neck flask. Stirring under 70° C., trimethyl chlorosilane (12.1 g, 111.1 mmol) was added under nitrogen protection and the mixture was stirred for 30 min. A solution of methyl 2,3α-hydroxy, 7-oxo-cholan-24-oate (compound 13 (10 g) in dry THF (50 ml)) was added drop-wise in 30 min, the mixture was then stirred for another 1 h under 70° C. Triethylamine (35.2 g, 348 mmol) was added at about −70° C. The mixture was kept stirring at −70° C. for another 1 h, then warmed to room temperature and stirred overnight. Cooled with ice and quenched with slow addition of sat. NaHCO₃ drop-wise. Extracted with ethyl acetate and the aqueous phase was extracted with EtOAc. The combined organic fraction was washed with sat. NaHCO$_3$ aq. solution and brine, dried with Na$_2$SO$_4$ and concentrated, and the crude product was purified by silica gel column chromatography (EA/PE=2%) to afford the target compound (12.9 g, yield 95%).

2. Synthesis of Methyl 3α-hydroxy-6-(ethylidene-d3)-7-keto-5β-cholan-24-oate (Compound 15)

Methyl 3α, 7-bis(trimethylsilyloxy)-5β-cholan-6-en-24-oate (11.0 g, 18.2 mmol) and dichloromethane (60 ml) was added to a four-neck flask, To a stirring mixture, (methyl-d3) aldehyde (2.1 ml, 36.4 mmol) was added under −40° C. Stirred at about −60° C. for 10 min, a solution of BF$_3$.OEt$_2$ (10 ml) in 20 ml of dichloromethane was added drop-wise. After stirring for another 3 h at −60° C., the mixture was naturally warmed to room temperature and stirred overnight. Cooled with ice and slowly quenched with sat. NaHCO$_3$ aqueous solution, stirred to mix and extracted. The aqueous phase was washed with dichloromethane (60 ml), and the combined organic fraction was added with 3N HCl aqueous solution and kept stirring for 1 h in ice-bath. The reaction was quenched with a saturated aqueous solution of NaHCO$_3$, extracted once more, and the aqueous layer was washed with dichloromethane. The combined organic layers were dried with Na$_2$SO$_4$ and concentrated, and the crude product was purified by silica gel column chromatography (EA/PE=25-35%), to afford the target compound (6.1 g, yield 70%).

3. Synthesis of Methyl 3α-hydroxy-6α-(ethyl-d$_3$)-7-keto-5β-cholan-24-oate (Compound 16)

Methyl 3α-hydroxy-6-(ethylidene-d3)-7-keto-5β-cholan-24-oate (0.18 g, 0.42 mmol), acetic acid (10 ml), concentrated HCl (0.5 ml) and platinum (IV) oxide (20 mg) was added. The mixture was charged with hydrogen and reacted for 12 h under hydrogen atmosphere at room temperature. Filtrated and concentrated to afford the target compound (0.17 g, 94%).

4. Synthesis of 3α-hydroxy-6α-(ethyl-d$_3$)-7-keto-5β-cholan-24-Acid (Compound 17)

To a reaction flask, methyl 3α-hydroxy-6α-(ethyl-d$_3$)-7-keto-5β-cholan-24-oate (0.17 g, 0.39 mmol), sodium hydroxide aq. solution (10%, 8.0 ml) and methanol/water (4.5/1, 11 ml) was added successively. The mixture was stirred for 16 h at 35° C., then concentrated. After addition of water, 1N HCl was added to adjust pH 2-3 and filtered. The cake was washed with pure water and dried to afford the target compound (0.14 g, 79%).

5. Synthesis of 3α, 7α-dihydroxy-6α-(ethyl-d$_3$)-7-d-5β-cholan-24-Acid (Compound 18)

3α-hydroxy-6α-(ethyl-d$_3$)-7-keto-5β-cholan-24-acid (65 mg, 0.15 mmol), sodium hydroxide aq. solution (50%, 200 mg) and water (3.0 ml) was added successively. Under stirring, sodium borodeuteride (13 mg, 0.3 mmol) was added and the mixture was stirred for 16 h at 100° C. Cooled to room temperature and added with 1N HCl to adjust pH 2-3. The precipitate was filtrated, washed with purified water and dried to afford the target compound (45 mg, 69%). $^1$H NMR (400 MHz, DMSO-d$_6$) δ: 11.95 (brs, 1H), 4.31 (s, J=4.0 Hz, 1H), 4.04 (d, J=8.0 Hz, 1H), 3.14-3.13 (m, 1H), 2.27-2.20 (m, 1H), 2.15-2.07 (m, 1H), 1.93-0.84 (m, 31H), 0.61 (s, 3H). ESI-MS (m/z): 425 (M+H)$^+$, 447 (M+Na)$^+$.

Example 5 Synthesis of 3α, 7α-Dihydroxy-6α-(Ethyl-d$_3$)-5β-Cholan-24-Oic Acid (Compound 19)

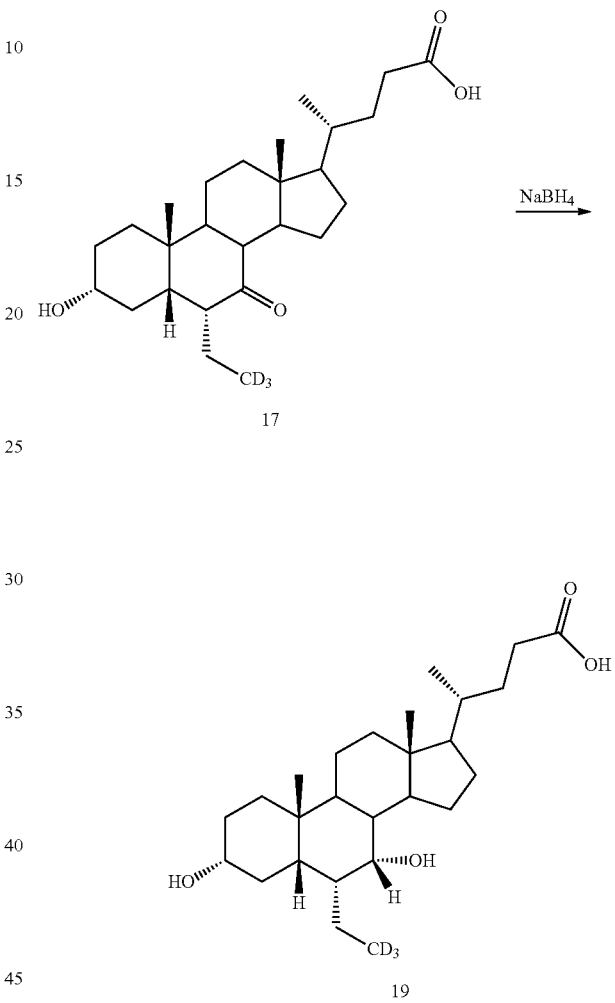

3α-hydroxy-6α-(ethyl-d$_3$)-7-keto-5β-cholan-24-acid (65 mg, 0.15 mmol) was added sodium hydroxide aq. solution (50%, 200 mg) and water (3.0 ml) were added successively into a reaction flask. Under stirring, sodium borohydride (13 mg, 0.3 mmol) was added and the mixture was stirred for 16 h at 100° C. Cooled down to room temperature and added 1N HCl to adjust pH 2-3. The precipitate was filtered, washed with purified water and dried to afford the target compound (51 mg, 78%). $^1$H NMR (400 MHz, DMSO-d$_6$) δ: 11.97 (brs, 1H), 4.32 (d, J=4.0 Hz, 1H), 4.07 (d, J=4.0 Hz, 1H), 3.50 (s, 1H), 3.14-3.13 (m, 1H), 2.27-2.20 (m, 1H), 2.15-2.07 (m, 1H), 1.93-0.84 (m, 31H), 0.61 (s, 3H). ESI-MS (m/z): 424 (M+H)$^+$, 446 (M+Na)$^+$.

Example 6 Synthesis of 3α, 7α-Dihydroxy-6α-(Ethyl-d₄)-7-d-5β-Cholan-24-Oic Acid (Compound 23)

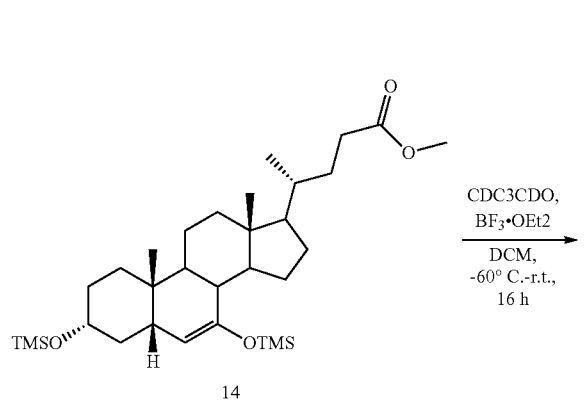

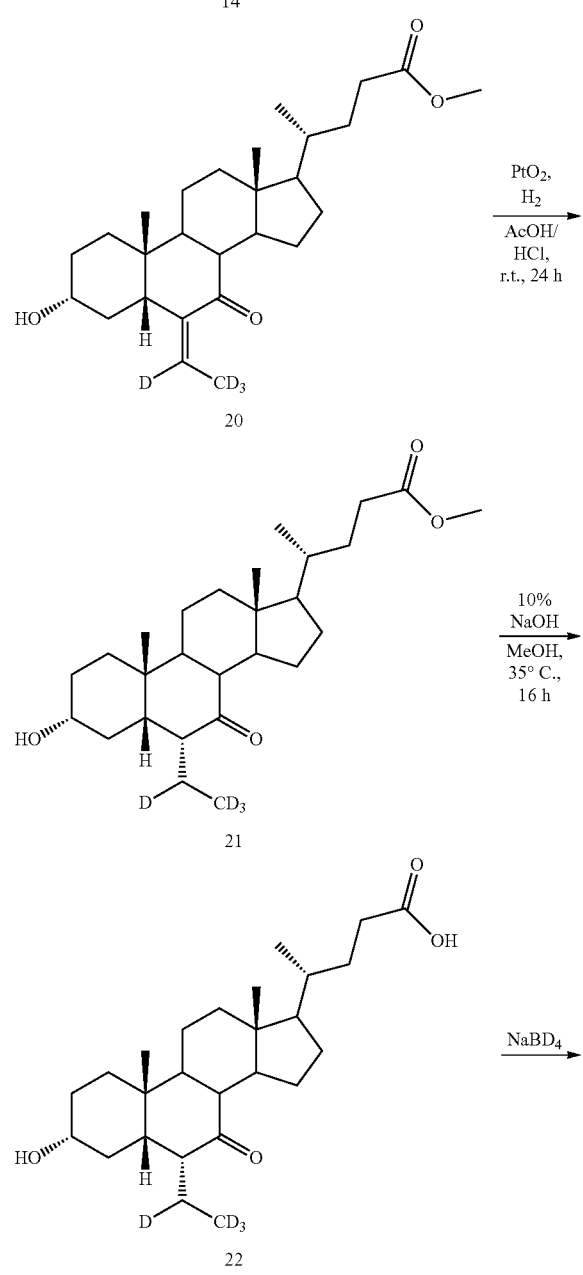

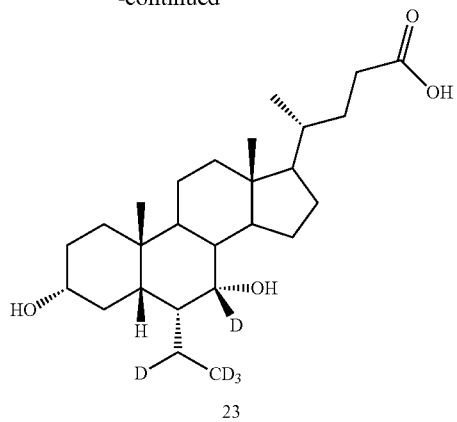

1. Synthesis of methyl 3α-hydroxy-6-(ethylidene-d₄)-7-keto-5β-cholan-24-oate (Compound 20)

Methyl 3α, 7-bis(trimethylsilyloxy)-5β-cholan-6-en-24-oate (11.0 g, 18.2 mmol) and dichloromethane (60 ml) were added successively into a four-neck flask, and acetaldehyde-d₄ (2.1 ml, 36.4 mmol) was added at −40° C. After stirring for 10 min at −60° C., a solution of BF₃·OEt₂ (10 ml) in dichloromethane (20 ml) was slowly added drop-wise. Stirred for another 3 h at −60° C. and naturally warmed to room temperature and stirred overnight. Under ice-bath, sat. NaHCO₃ was slowly added and stirred to mix. and the mixture was extracted and the aqueous layer was washed with dichloromethane. The combined organic fraction was added with 3N HCl and kept stirring for 1 h under ice bath. The mixture was quenched with a saturated aqueous solution of NaHCO₃, extracted once more, and the aqueous layer was washed with dichloromethane. The combined organic layer was dried with anhydrous Na₂SO₄ and concentrated. The crude product was purified by silica gel column chromatography (EtOAc/Petroleum=25-35%) to afford the target compound (5.2 g, yield 59%).

2. Synthesis of methyl 3α-hydroxy-6α-(ethyl-d₄)-7-keto-5β-cholan-24-oate (Compound 21)

To a solution of methyl 3α-hydroxy-6-(ethylidene-d₄)-7-keto-5β-cholan-24-oate (0.18 g, 0.42 mmol) in acetic acid (10 ml) and conc. HCl (0.5 ml) and platinum (IV) oxide (20 mg) were added. The mixture was charged with hydrogen and stirred under hydrogen atmosphere for 12 h at room temperature. Filtrated and concentrated to afford the target compound (0.16 g, 88%).

3. Synthesis of 3α-hydroxy-6α-(ethyl-d₄)-7-keto-5β-cholan-24-Acid (Compound 22)

Methyl 3α-hydroxy-6α-(ethyl-d₄)-7-keto-5β-cholan-24-oate (0.16 g, 0.36 mmol), sodium hydroxide aq. solution (10%, 8.0 ml) and methanol/water (4.5/1, 11 ml) was added. The mixture was stirred for 16 h at 35° C. Concentrated and added with water. 1N HCl was added to adjust pH 2-3. The precipitate was filtered, washed with purified water and dried to afford the target compound (0.12 g, 73%).

4. Synthesis of 3α,7α-dihydroxy-6α-(ethyl-d₄)-7-d-5β-cholan-24-Acid (Compound 23)

3α-hydroxy-6α-(ethyl-d₄)-7-keto-5β-cholan-24-acid (60 mg, 0.14 mmol), sodium hydroxide aq. solution (50%, 200 mg) and water (3.0 ml) were added successively into a flask. Under stirring, sodium borodeuteride (13 mg, 0.3 mmol) was added and the mixture was stirred for 16 h at 100° C. Cooled down to room temperature and added 1N HCl to adjust pH 2-3. The precipitate was filtered, washed with purified water and dried to afford the target compound (40 mg, 67%). $^1$H NMR (400 MHz, DMSO-$d_6$) δ: 11.97 (brs, 1H), 4.32 (s, 1H), 4.07 (d, J=8.0 Hz, 1H), 3.16-3.11 (m, 1H), 2.28-2.19 (m, 1H), 2.15-2.07 (m, 1H), 1.93-0.84 (m, 30H), 0.61 (s, 3H). ESI-MS (m/z): 426 (M+H)$^+$, 448 (M+Na)$^+$.

Example 7 Synthesis of 3α, 7☐-Dihydroxy-6α-(Ethyl-$d_4$)-5β-Cholan-24-Acid (Compound 24)

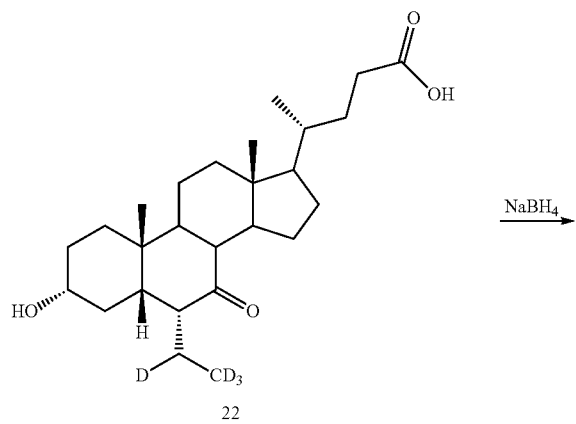

3α-hydroxy-6α-(ethyl-$d_4$)-7-keto-5β-cholan-24-acid (30 mg, 0.07 mmol), sodium hydroxide aq. solution (50%, 50 mg) and water (2.0 ml) were added into a flask. Under stirring, sodium borohydride (10 mg, 0.15 mmol) was added and the mixture was stirred for 16 h at 100° C. Cooled down to room temperature and added 1N HCl to adjust pH 2-3. The precipitate was filtered, washed with purified water and dried to afford the target compound (22 mg, 70%). $^1$H NMR (400 MHz, DMSO-$d_6$) δ: 11.97 (brs, 1H), 4.32 (d, J=4.0 Hz, 1H), 4.07 (d, J=4.0 Hz, 1H), 3.50 (s, 1H), 3.14-3.13 (m, 1H), 2.27-2.20 (m, 1H), 2.15-2.07 (m, 1H), 1.93-0.84 (m, 30H), 0.61 (s, 3H). ESI-MS (m/z): 425 (M+H)$^+$, 447 (M+Na)$^+$.

Example 8 Synthesis of 3α,7α-Dihydroxy-6α-Ethyl-7,23,23-$d_3$-5β-Cholan-24-Acid (Compound 25)

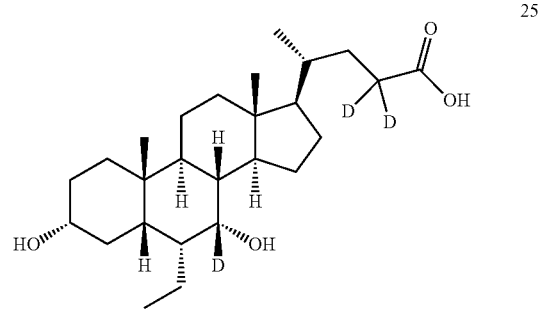

3α,7α-dihydroxy-6α-ethyl-7-d-5β-cholan-24-oic acid (0.2 g) was dissolved in sodium deuteroxide in deuterium oxide. The mixture was stirred for 24 h at room temperature. After removal of the solvents under highly vacuum, the residue was dissolved in sodium deuteroxide in deuterium oxide. The mixture was kept stirring for another 24 h at room temperature. 3N HCl was added to adjust pH 2-3, and extracted with ethyl acetate. The combined organic phase was washed subsequently with purified water and brine, dried with $Na_2SO_4$ and filtered. The filtrate was concentrated and the residue was purified by silica gel column chromatography (5% methanol/dichloromethane) to afford the target compound. ESI-MS (m/z): 424 (M+H)$^+$, 446 (M+Na)$^+$.

Example 9 Pharmacokinetic Evaluation in Rats

Male Sprague-Dawley rats, 7-8 weeks old, of which the body weight was about 210 g, 6 rats per group, duodenal administrated with 1 umol/min/kg dose of (a) control group: obeticholic acid, or (b) test group: the compounds prepared in examples 1 to 8. Administrated for 1 hour, of which the flow rate of administration was 2.5 mL/h. The plasma pharmacokinetics and bile excretion kinetics were compared.

Rats were fed with standard feed and given water. 16 hours of fasting before the test began. The drug was dissolved with physiological saline. Blood was corrected from left femoral vein. The time of blood collection was 0.5 hours before administration, 0.5 hours, 1 hour, 1.5 hours, 2 hours, 2.5 hours, 3 hours and 3.5 hours after administration. Bile was collected during and 2.5 hours after administration at intervals of 15 min.

Plasma and bile were stored at −70° C. before analysis. The concentration of the compounds of the invention in plasma and bile was determined by LC-MS/MS. Pharmacokinetic parameters were calculated based on the plasma concentration of each animal at different time points and the concentration of the drug in the bile.

As a result, it was found that the compound of the present invention had higher plasma exposure and biliary secretion in the animal when compared to the control compound Aobelic acid, thus having better pharmacodynamics and therapeutic effect.

Example 10 In Vitro Pharmacodynamic Evaluation of the Compounds of the Present Invention for Farnesol Alcohol X Receptor (FXR)

The farnesoid X receptor (FXR) activation of the compounds of the present invention is determined by Recruitment Coactivator Assay, i.e. AlphaScreen. Specific in vitro pharmacodynamic evaluation experimental program has referred to the literature J Pharmacol Exp Ther 350:56-68, July 2014.

The experimental results are shown in Table 1. It can be seen that the compounds of the present invention have excellent activating activity to the farnesoid X receptor (FXR).

TABLE 1

| Compound | activating activity ($EC_{50}$) for FXR |
|---|---|
| chenodeoxycholic acid | >10000 nM, <20000 nM |
| obeticholic acid | <300 nM |
| Example 1 | <200 nM |
| Example 2 | <200 nM |
| Example 3 | <200 nM |
| Example 4 | <200 nM |
| Example 5 | <200 nM |
| Example 6 | <200 nM |
| Example 7 | <200 nM |
| Example 8 | <200 nM |

Example 11 Pharmaceutical Composition

| | |
|---|---|
| The compounds (Examples 1 to 8) | 10 g |
| Sodium carboxymethyl starch | 12 g |
| Microcrystalline cellulose | 180 g |

The above substances are mixed by conventional methods, and then filled into general gelatin capsules to obtain 1000 capsules.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

What we claim is:

1. A deuterated chenodeoxycholic acid derivative represented by formula (I) or a pharmaceutically acceptable salt thereof:

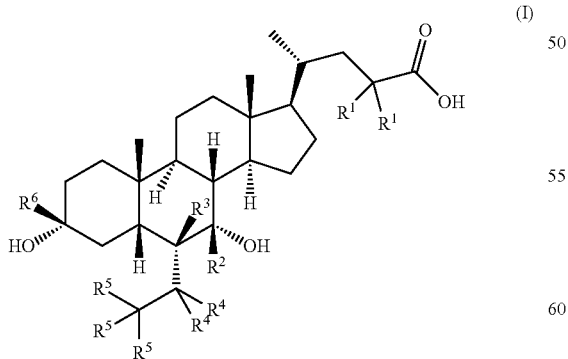

wherein:
$R^1$, $R^3$, $R^4$, $R^5$ and $R^6$ are each independently hydrogen or deuterium; and
$R^2$ is deuterium.

2. The compound of claim 1, wherein each of $R^1$ and $R^2$ is deuterium.

3. A compound selected from the group consisting of:

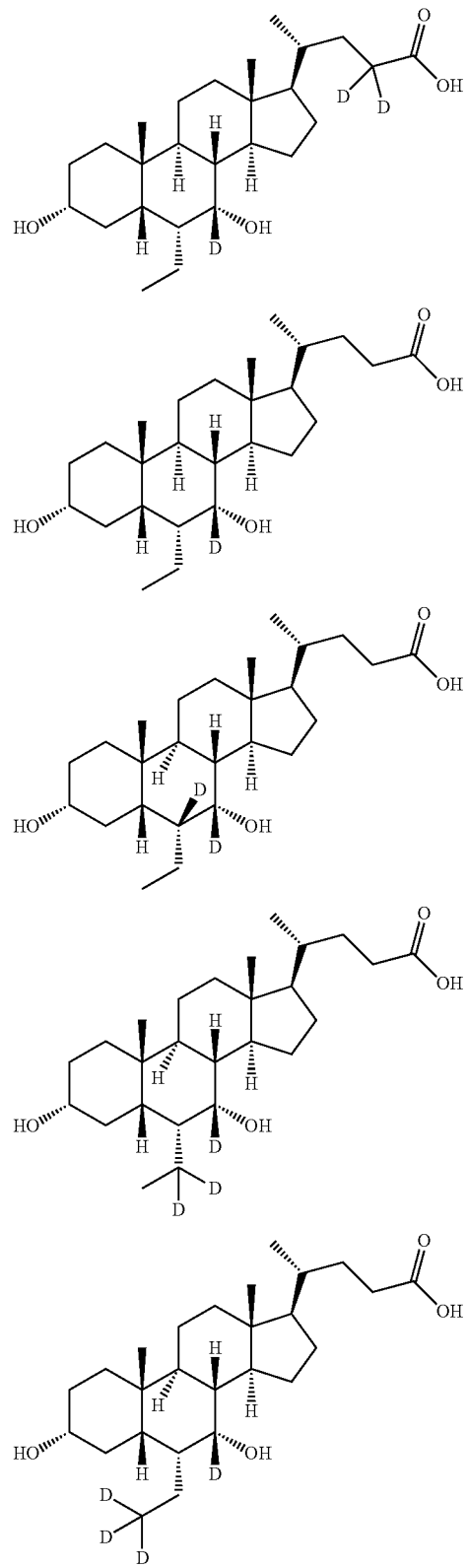

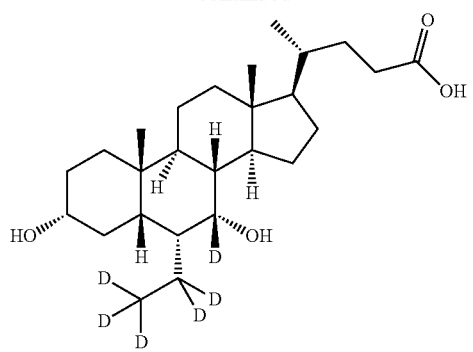
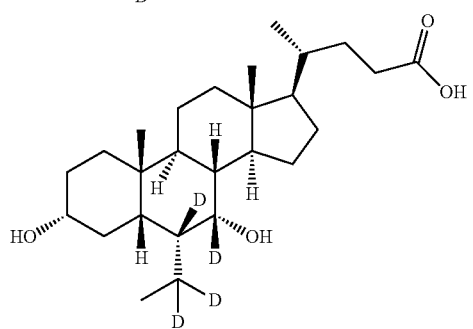
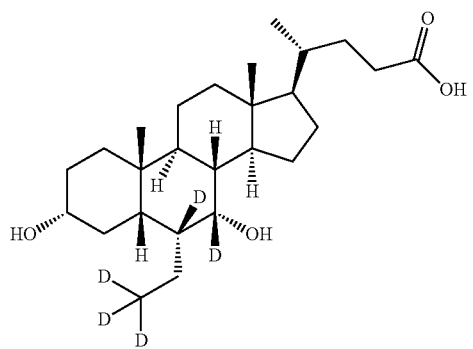
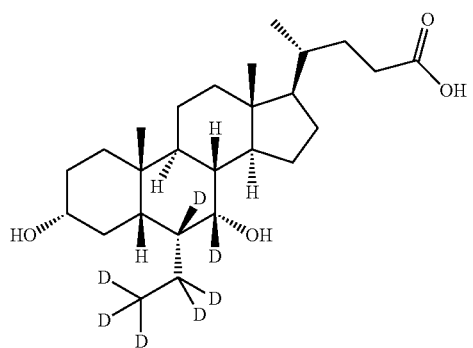
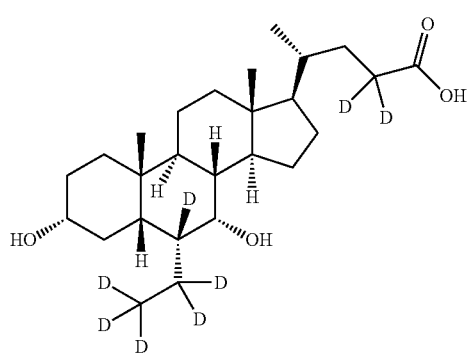
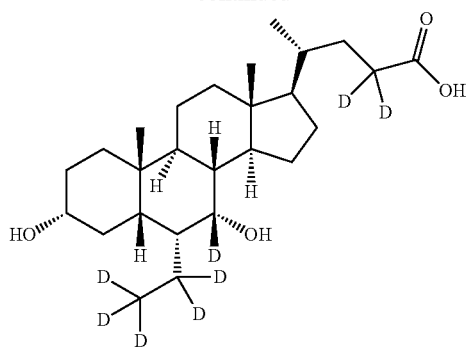
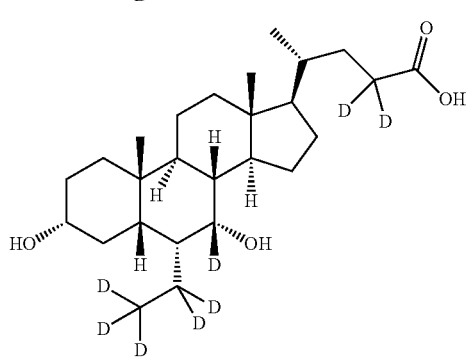
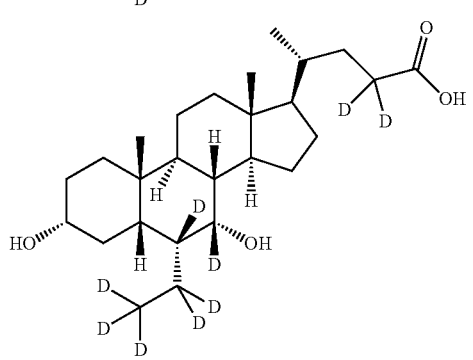
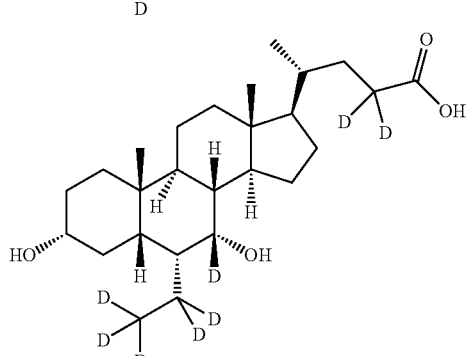
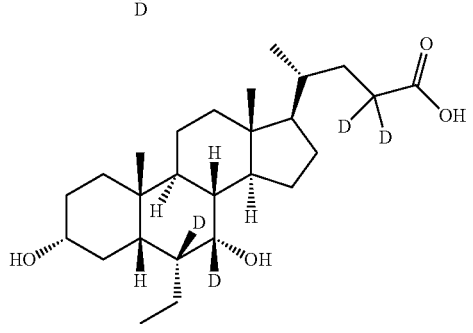

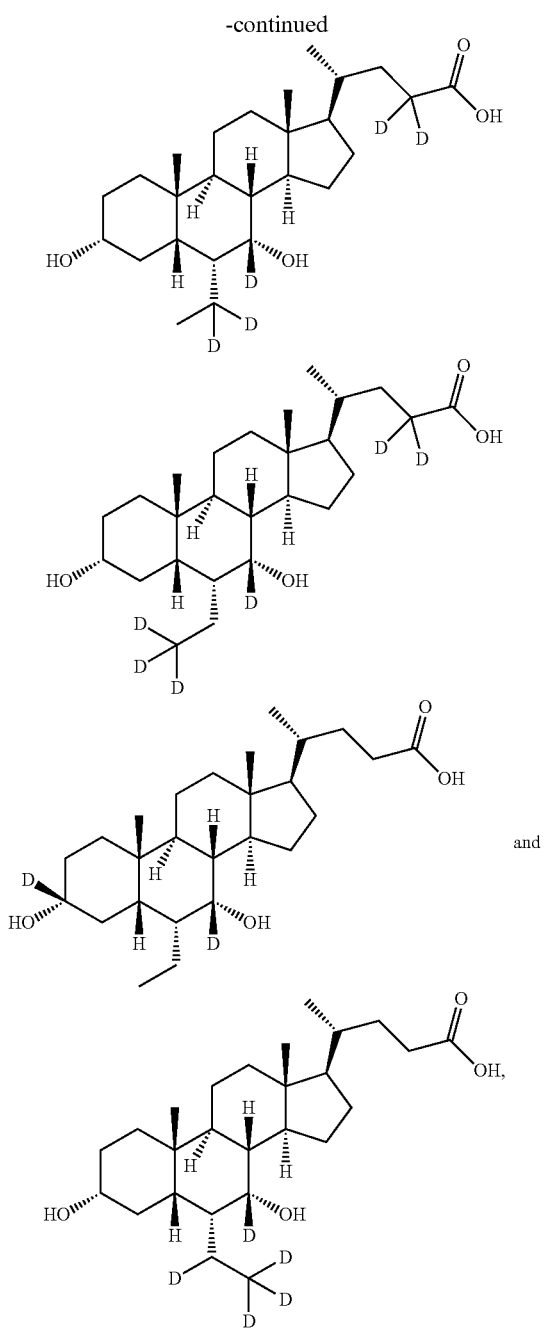

or a pharmaceutically acceptable salt thereof.

4. A pharmaceutical composition comprising a pharmaceutically acceptable carrier and the compound according to claim 1, or a pharmaceutically acceptable salt thereof.

5. The pharmaceutical composition of claim 4, further comprising an additional therapeutic agent, wherein the additional therapeutic agent is a medicine for treating cancer, cardiovascular disease, inflammation, infection, immune diseases, or metabolic diseases.

6. The pharmaceutical composition according to claim 4, wherein the pharmaceutical composition is formulated as an injectable, capsule, tablet, pill, powder or granules.

7. The pharmaceutical composition according to claim 5, wherein the additional therapeutic agent is selected from the group consisting of sorafenib, regorafenib, duonafenib, cisplatin, doxorubicin, gemcitabine, FOLFOX, decitabine, capecitabine, statins, rosiglitazone, pioglitazone, metformin, acarbose, voglibose, sulfonylureas, dipeptidyl peptidase-4 (DPP-4) inhibitors hypoglycemic agents, sodium-dependent glucose transporters (SGLT2) inhibitor hypoglycemic agents, glucagon-like peptide-1 (GLP-1) receptor agonists, interferon, pegylated interferon, anti-hepatitis C drugs, and anti-hepatitis B drugs.

8. A method of treating a disease related to farnesoid X receptor (FXR) and/or G-protein coupled bile acid receptor (GPBAR or TGR5) in a subject in need thereof, the method comprising administering to the subject the pharmaceutical composition according to claim 4, wherein the disease is selected from the group consisting of nonalcoholic steatohepatitis, nonalcoholic fatty liver disease, gallstones, primary biliary cirrhosis, cirrhosis, liver fibrosis, diabetes, atherosclerosis, and obesity.

9. The method according to claim 8, wherein the disease is selected from the group consisting of nonalcoholic steatohepatitis, nonalcoholic fatty liver disease, primary biliary cirrhosis, cirrhosis, liver fibrosis, diabetes, atherosclerosis and obesity.

10. The method according to claim 8, wherein the disease is selected from the group consisting of nonalcoholic steatohepatitis and primary biliary cirrhosis.

11. A pharmaceutical composition comprising a pharmaceutically acceptable carrier and the compound according to claim 3, or a pharmaceutically acceptable salt thereof.

12. The pharmaceutical composition of claim 11, further comprising an additional therapeutic agent, wherein the additional therapeutic agent is a medicine for treating cancer, cardiovascular disease, inflammation, infection, immune diseases, or metabolic diseases.

13. The pharmaceutical composition according to claim 11, wherein the pharmaceutical composition is formulated as an injectable, capsule, tablet, pill, powder or granule.

14. The pharmaceutical composition according to claim 12, wherein the additional therapeutic agent is selected from the group consisting of sorafenib, regorafenib, duonafenib, cisplatin, doxorubicin, gemcitabine, FOLFOX, decitabine, capecitabine, statins, rosiglitazone, pioglitazone, metformin, acarbose, voglibose, sulfonylureas, dipeptidyl peptidase-4 (DPP-4) inhibitors hypoglycemic agents, sodium-dependent glucose transporters (SGLT2) inhibitor hypoglycemic agents, glucagon-like peptide-1 (GLP-1) receptor agonists, interferon, pegylated interferon, anti-hepatitis C drugs, and anti-hepatitis B drugs.

15. A method of treating a disease related to farnesoid X receptor (FXR) and/or G-protein coupled bile acid receptor (GPBAR or TGR5) in a subject in need thereof, the method comprising administering to the subject the pharmaceutical composition according to claim 11, wherein the disease is selected from the group consisting of nonalcoholic steatohepatitis, nonalcoholic fatty liver disease, gallstones, primary biliary cirrhosis, cirrhosis, liver fibrosis, diabetes, atherosclerosis, and obesity.

16. The method according to claim 15, wherein the disease is selected from the group consisting of nonalcoholic steatohepatitis, nonalcoholic fatty liver disease, primary biliary cirrhosis, cirrhosis, liver fibrosis, diabetes, atherosclerosis and obesity.

17. The method according to claim 15, wherein the disease is selected from the group consisting of nonalcoholic steatohepatitis and primary biliary cirrhosis.

* * * * *